US011944734B2

(12) United States Patent
Katayama

(10) Patent No.: US 11,944,734 B2
(45) Date of Patent: Apr. 2, 2024

(54) BLOOD PURIFICATION APPARATUS

(71) Applicant: Nikkiso Company Limited, Tokyo (JP)

(72) Inventor: Yuki Katayama, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 111 days.

(21) Appl. No.: 17/489,899

(22) Filed: Sep. 30, 2021

(65) Prior Publication Data

US 2022/0016326 A1 Jan. 20, 2022

Related U.S. Application Data

(63) Continuation of application No. PCT/JP2020/018303, filed on Apr. 30, 2020.

(30) Foreign Application Priority Data

May 9, 2019 (JP) .................................. 2019-089299

(51) Int. Cl.
*A61M 1/34* (2006.01)
*A61M 1/16* (2006.01)
*A61M 1/36* (2006.01)

(52) U.S. Cl.
CPC ........ *A61M 1/3451* (2014.02); *A61M 1/1654* (2013.01); *A61M 1/3606* (2014.02); *A61M 1/3638* (2014.02)

(58) Field of Classification Search
None
See application file for complete search history.

(56) References Cited

U.S. PATENT DOCUMENTS

2017/0296727 A1 10/2017 Burbank et al.
2017/0326294 A1* 11/2017 Kato ......................... F16B 2/10
(Continued)

FOREIGN PATENT DOCUMENTS

JP 2011-200407 A 10/2011
JP 2017-006539 A 1/2017
(Continued)

OTHER PUBLICATIONS

International Search Report for Application No. PCT/JP2020/018303, dated Jul. 14, 2020.

*Primary Examiner* — Krishnan S Menon
(74) *Attorney, Agent, or Firm* — Young Basile Hanlon & MacFarlane, P.C.

(57) ABSTRACT

A blood purification apparatus that includes a blood circuit including an arterial blood circuit and a venous blood circuit and through which blood of a patient is allowed to extracorporeally circulate; a blood purification unit connected to and provided between the arterial blood circuit and the venous blood circuit and that purifies the blood flowing through the blood circuit; a blood pump provided to the arterial blood circuit and that delivers the blood of the patient from a distal end of the arterial blood circuit to a distal end of the venous blood circuit; a substitution line through which a substitution fluid is allowed to be introduced into the blood circuit; and an infusion portion attached to the substitution line and from which a predetermined liquid drug to be administered to the patient is allowed to be infused into the substitution line. The blood purification apparatus includes a control unit that executes a drug introduction mode in which the substitution fluid in the substitution line is introduced into the blood circuit, the control unit causing the liquid drug infused from the infusion portion in the drug introduction mode to be introduced into the blood circuit together with the substitution fluid; and (Continued)

a calculation unit that calculates a volume of the substitution fluid introduced from the substitution line into the blood circuit with the execution of the drug introduction mode.

16 Claims, 21 Drawing Sheets

(56) References Cited

U.S. PATENT DOCUMENTS

2018/0036470 A1\* 2/2018 Hasegawa .............. A61M 1/301
2019/0201609 A1\* 7/2019 Ichikawa ............ A61M 1/3646

FOREIGN PATENT DOCUMENTS

WO 2011/039306 A1 4/2011
WO WO-2011118701 A1 \* 9/2011 .............. A61M 1/16

\* cited by examiner

[Fig. 1]
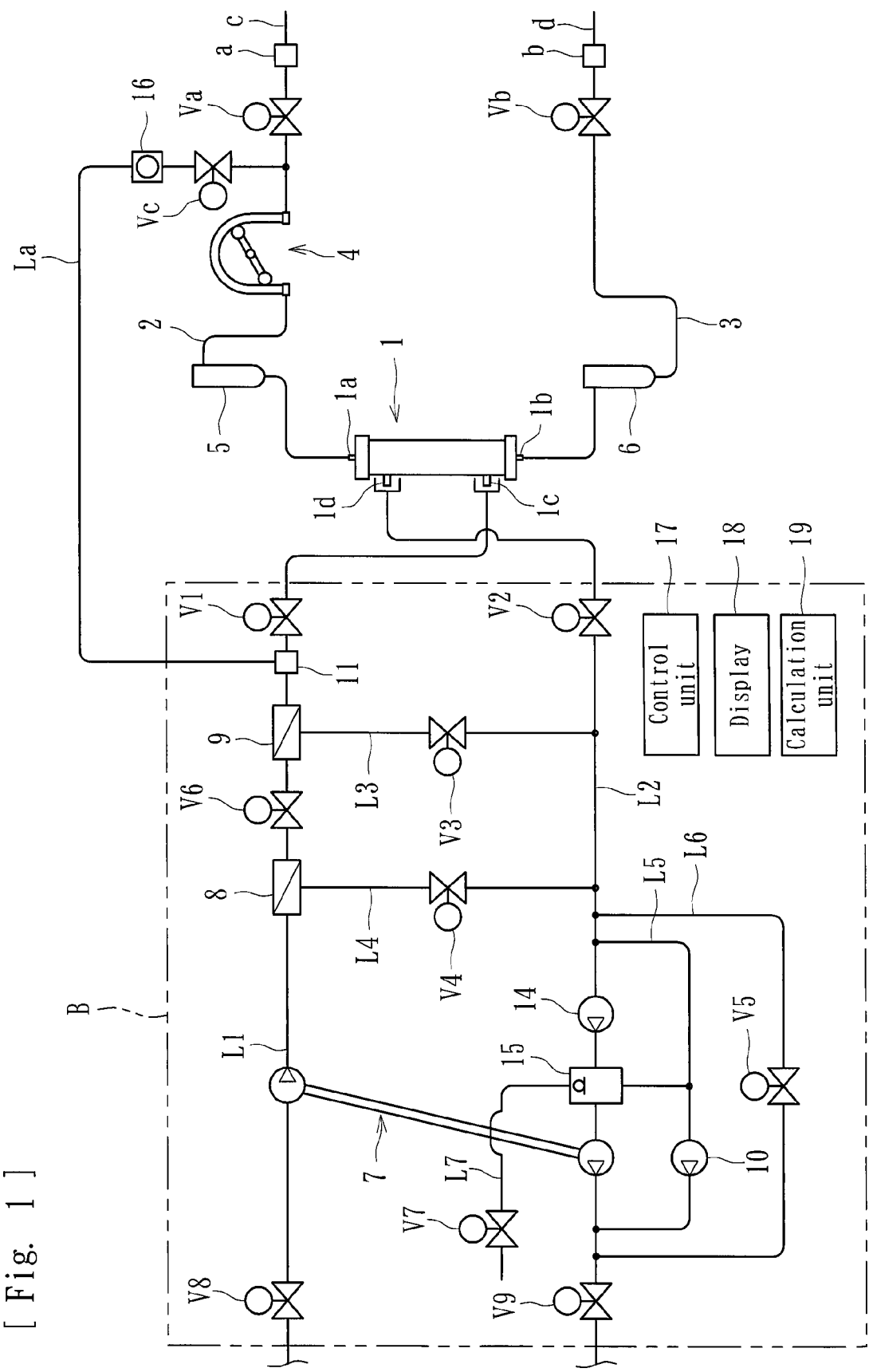

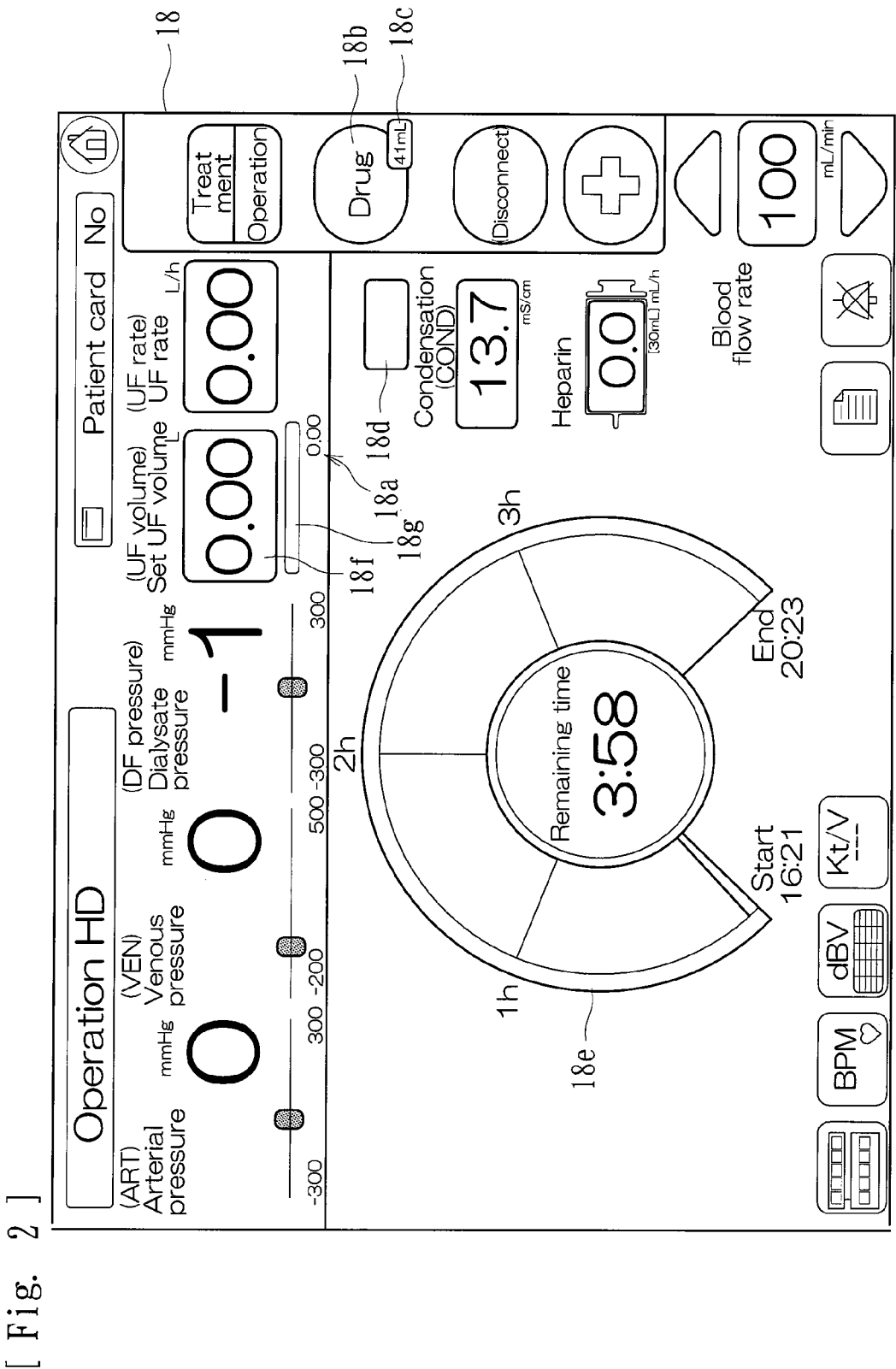
[Fig. 2]

[Fig. 3]
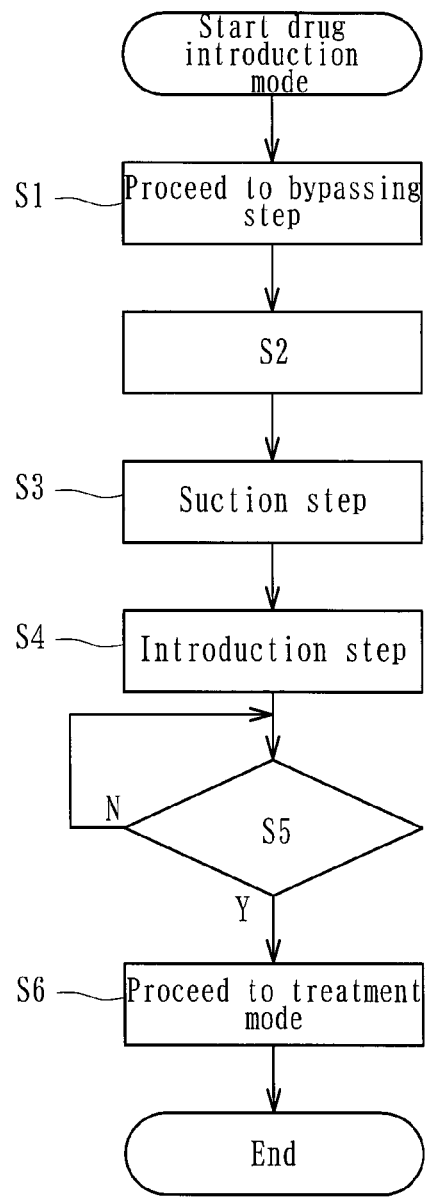
(S2) Negative pressure-generating step
 (Pressure-controlling step)
(S5) Has preset volume of substitution fluid been introduced?

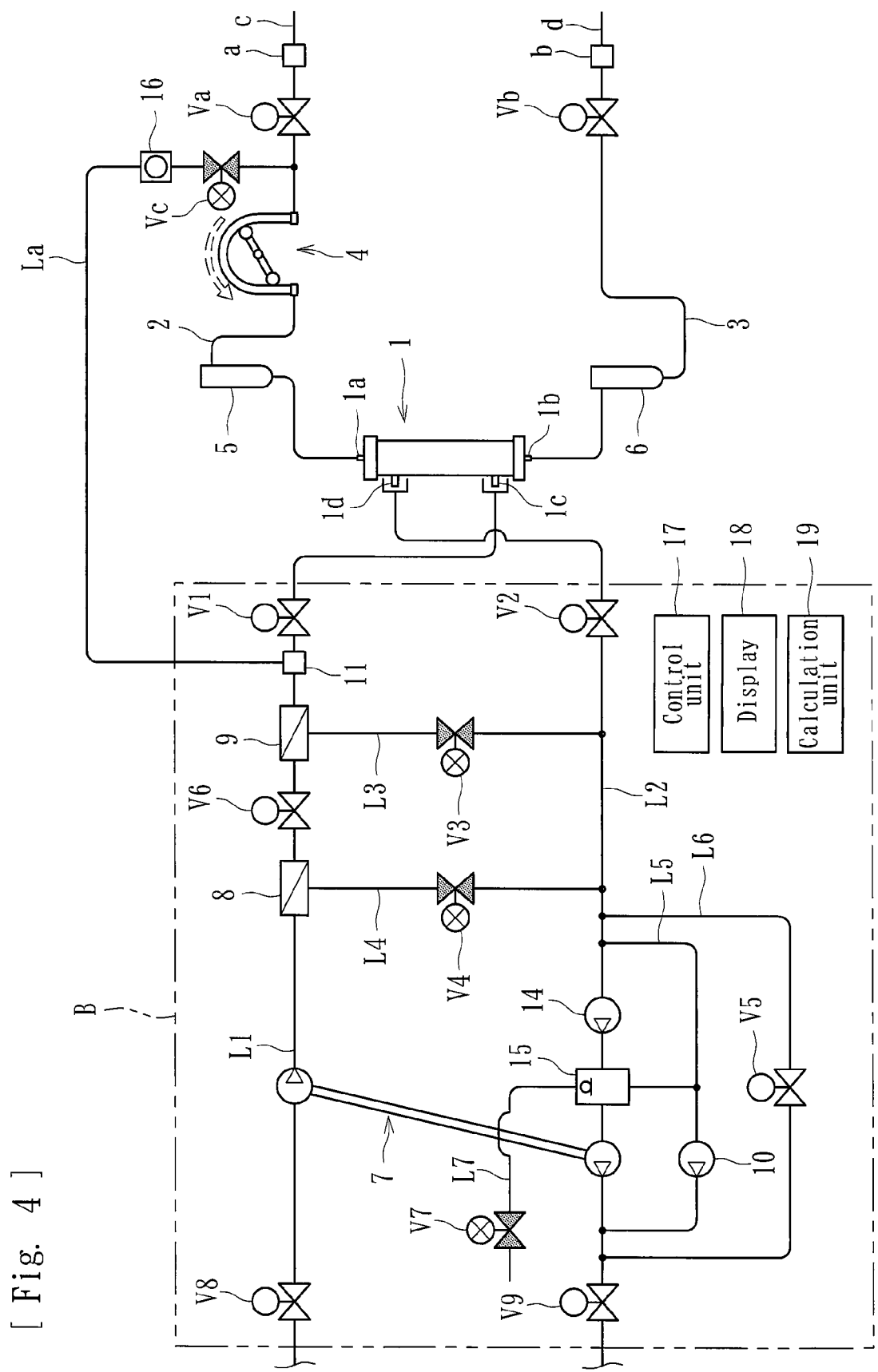
[Fig. 4]

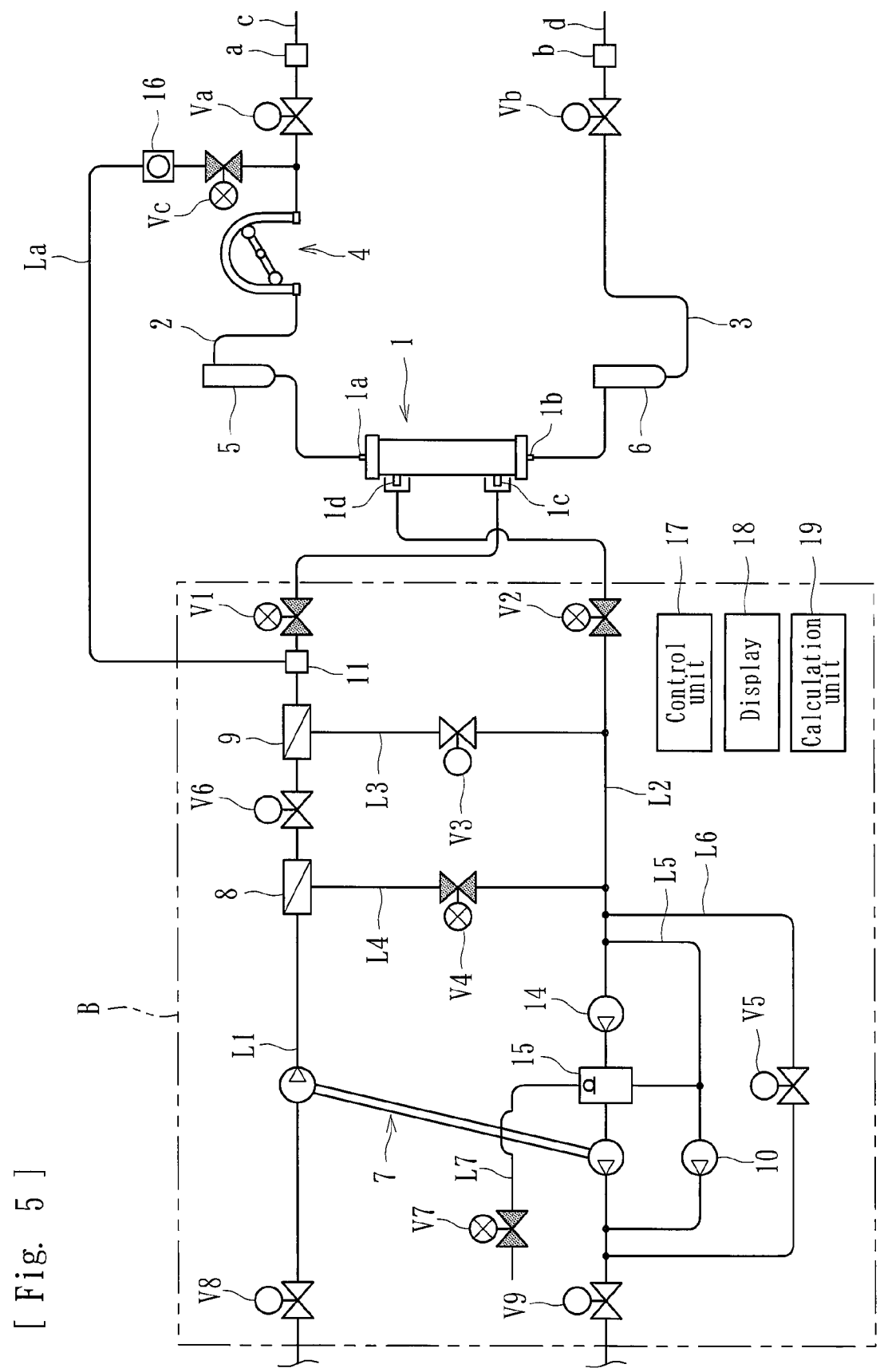
[Fig. 5]

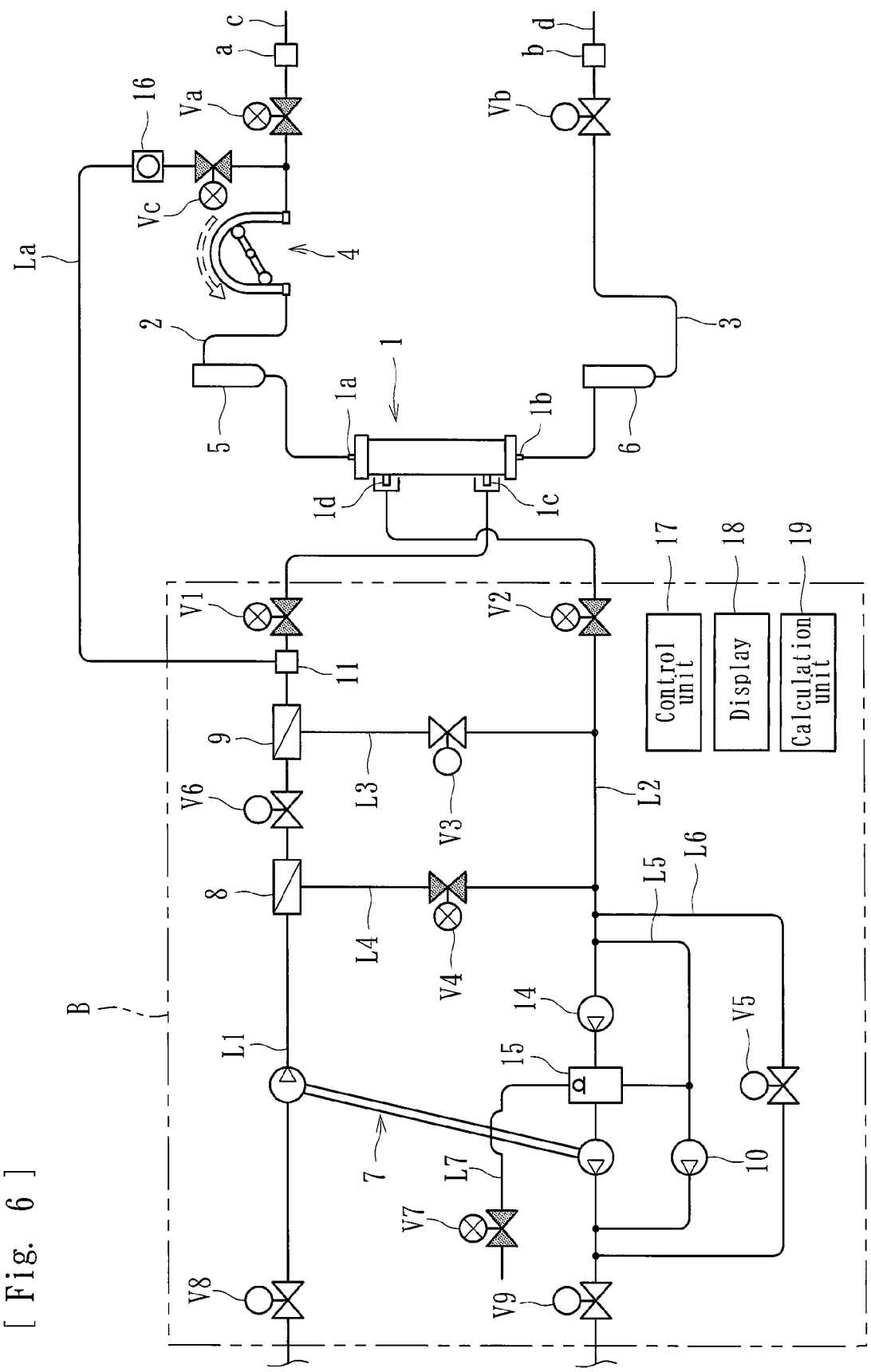
[Fig. 6]

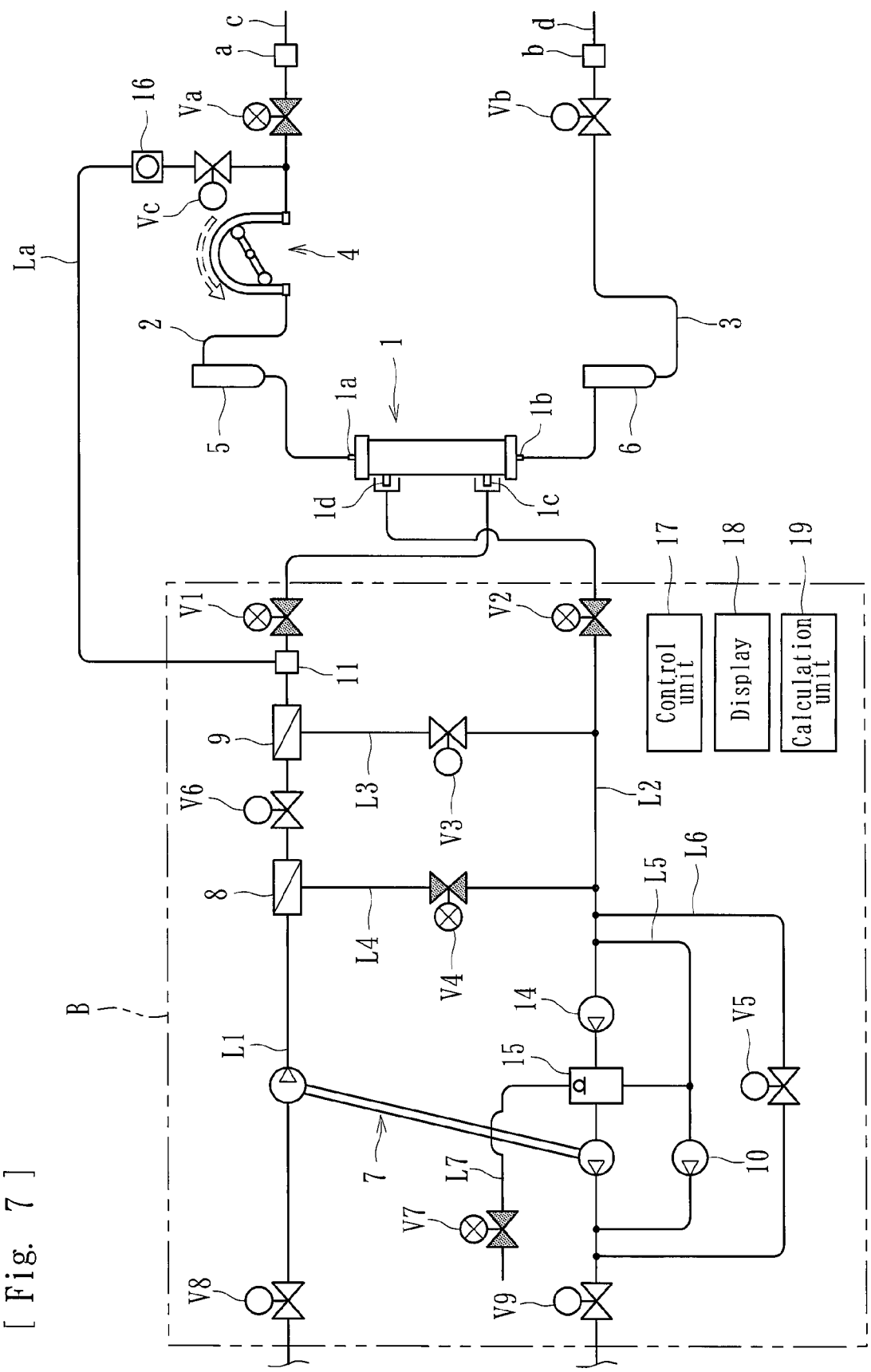
[Fig. 7]

[Fig. 8]
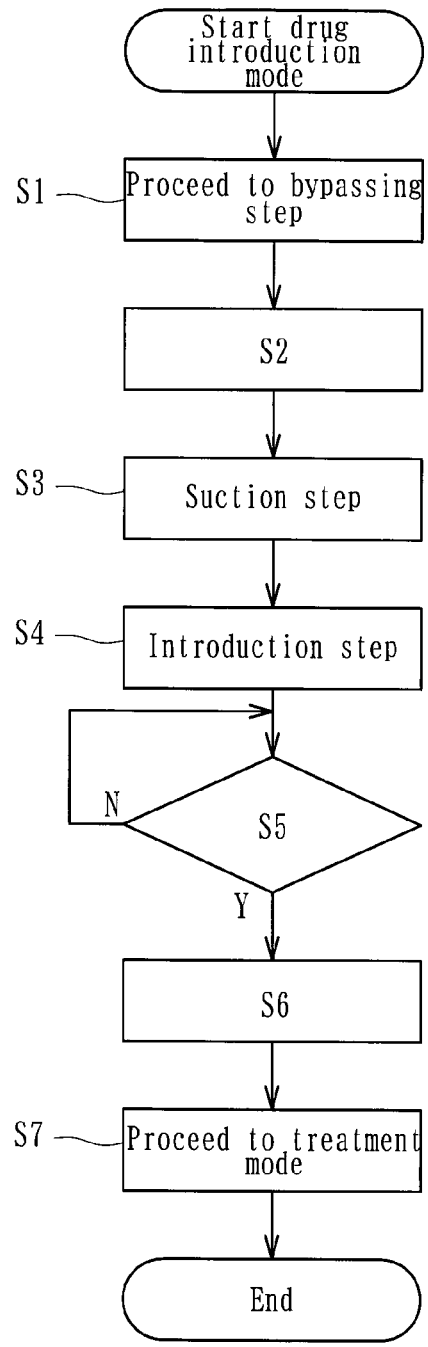
(S2) Negative pressure-generating step
(Pressure-controlling step)
(S5) Has preset volume of substitution fluid been introduced?
(S6) Correct target ultrafiltration volume

[ Fig. 9 ]
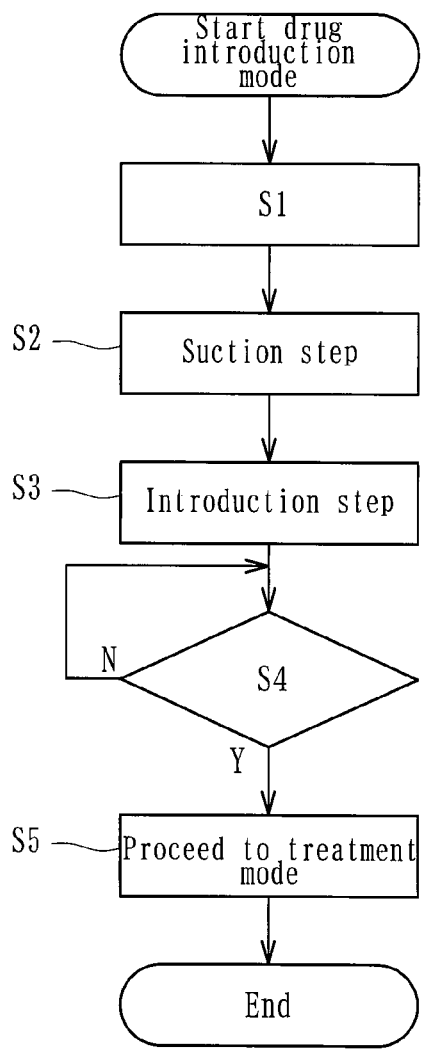
(S1) Negative pressure-generating step
 (Pressure-controlling step)
(S4) Has preset volume of substitution fluid
 been introduced?

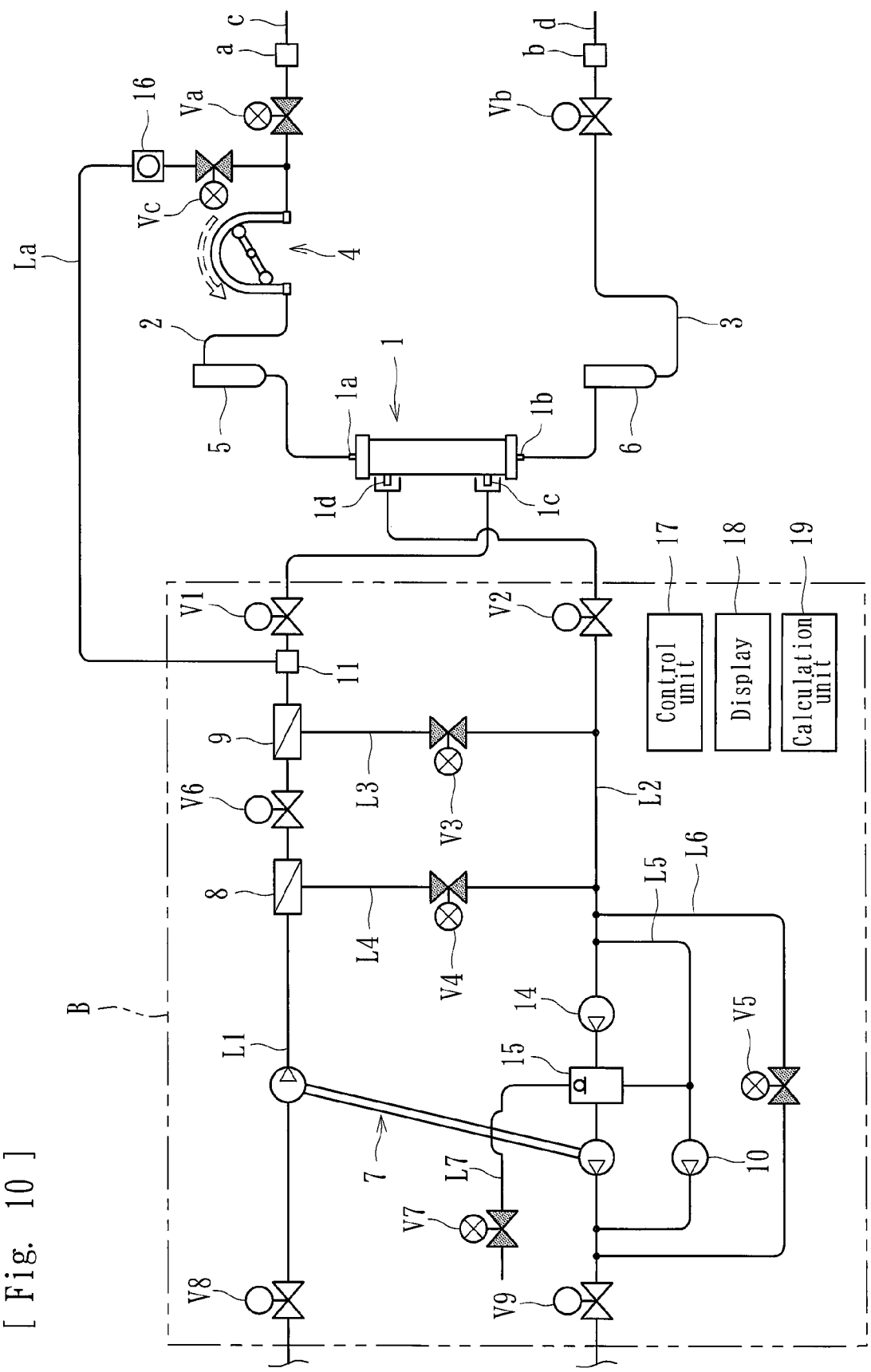
[Fig. 10]

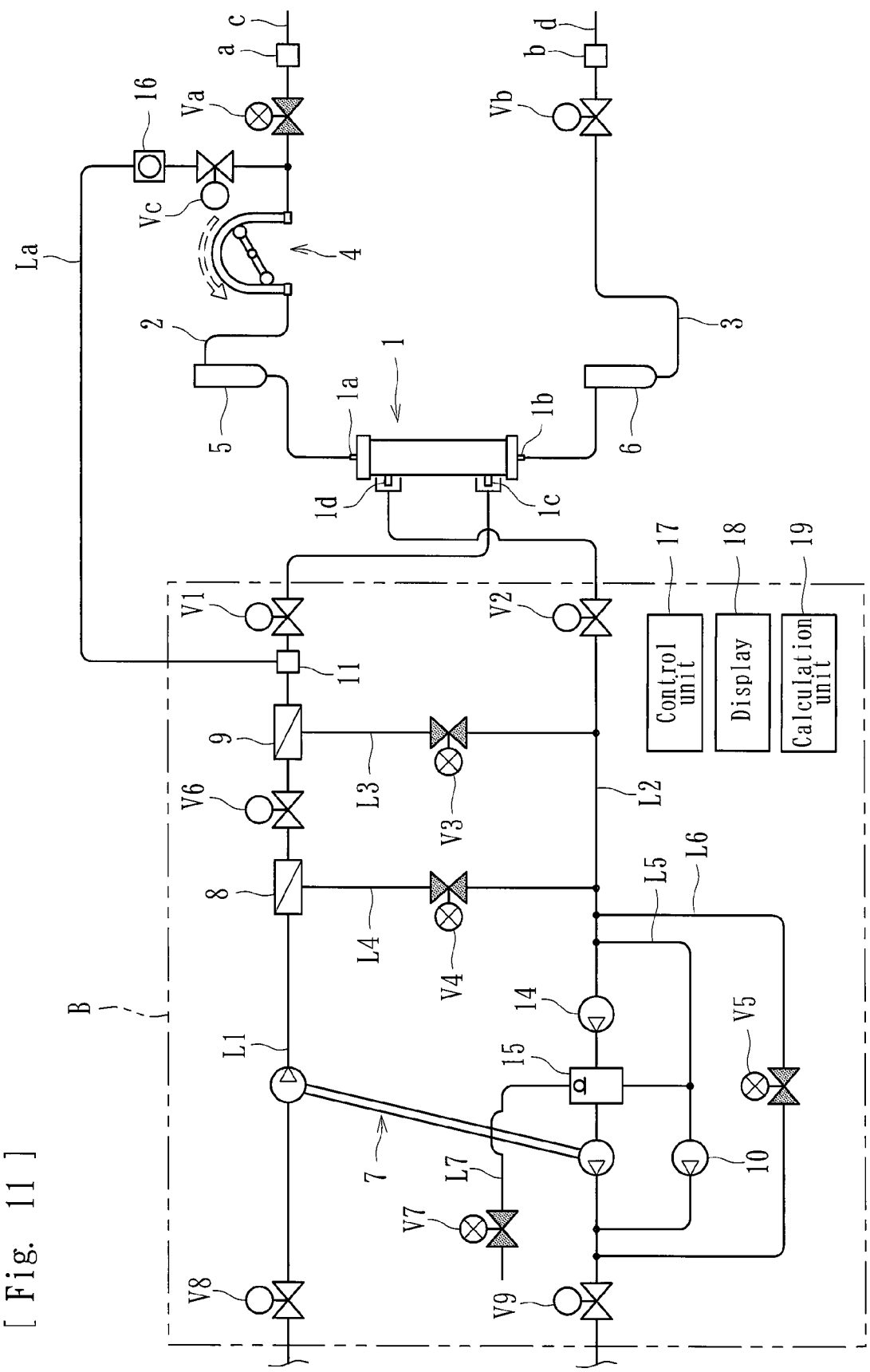
[Fig. 11]

[ Fig. 12 ]
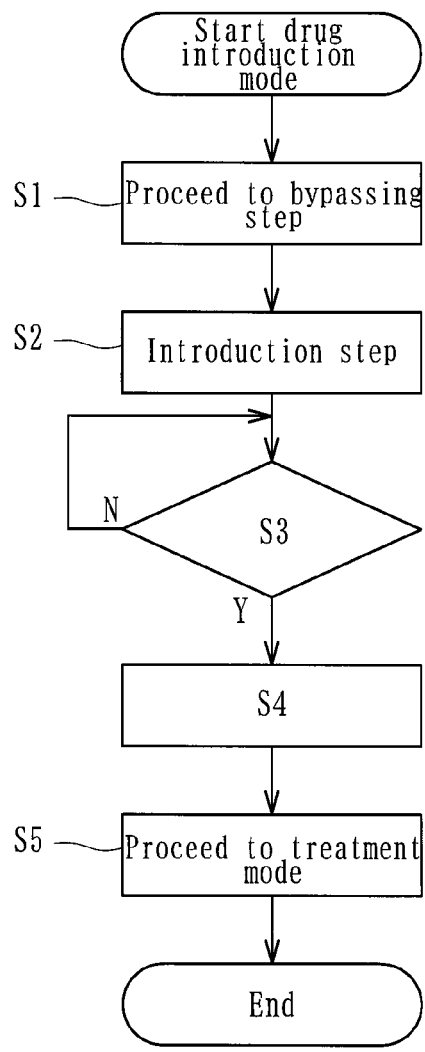
(S3) Has preset volume of substitution fluid been introduced?
(S4) Correct target ultrafiltration volume

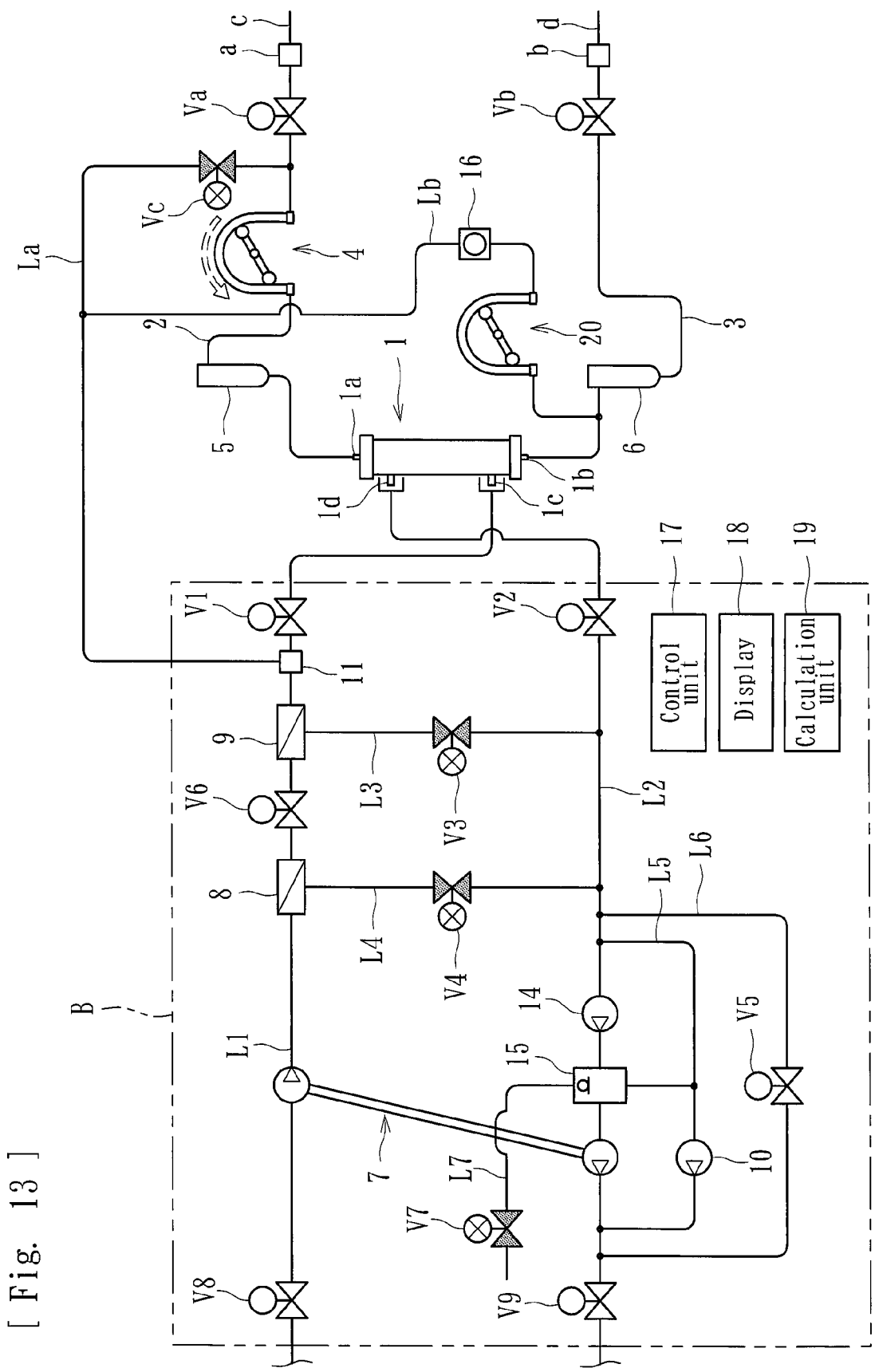
[Fig. 13]

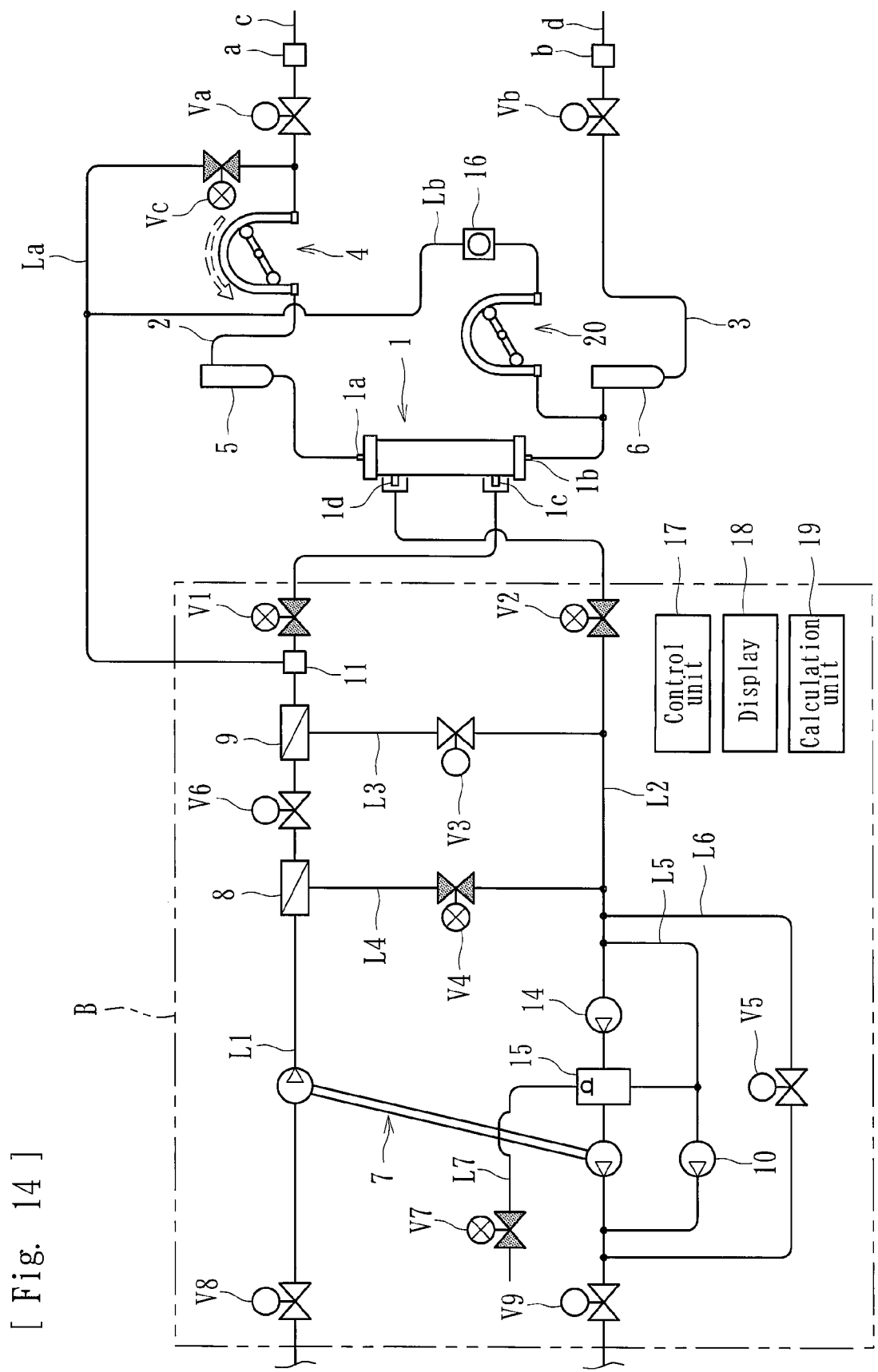
[Fig. 14]

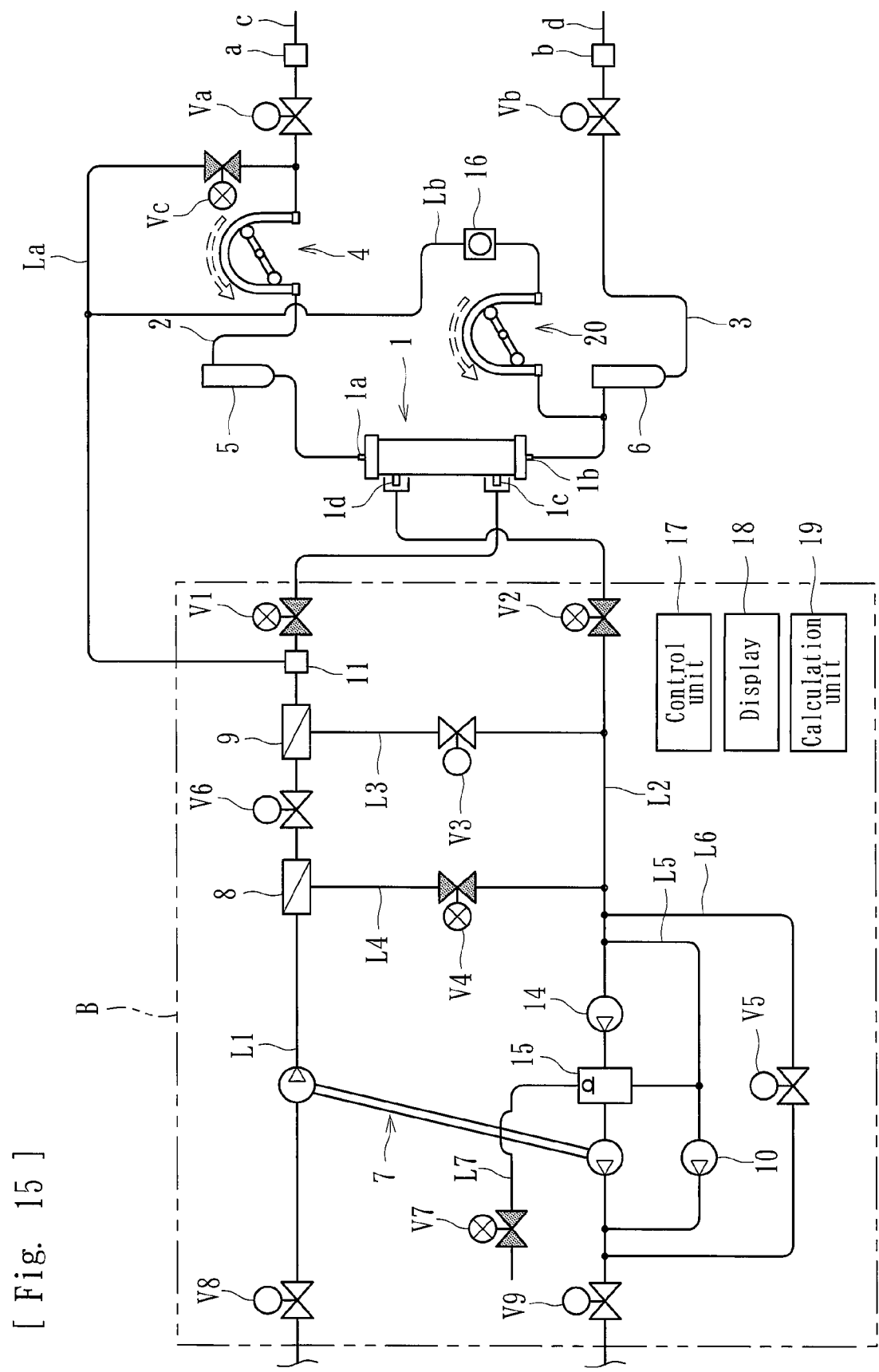
[Fig. 15]

[ Fig. 16 ]
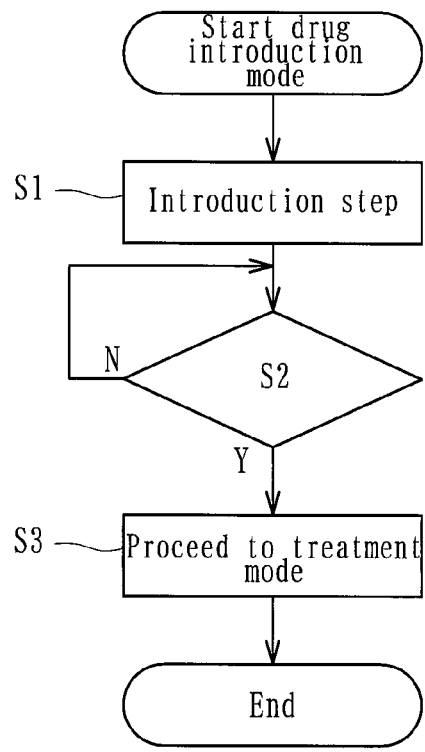
(S2) Has preset volume of substitution fluid been introduced?

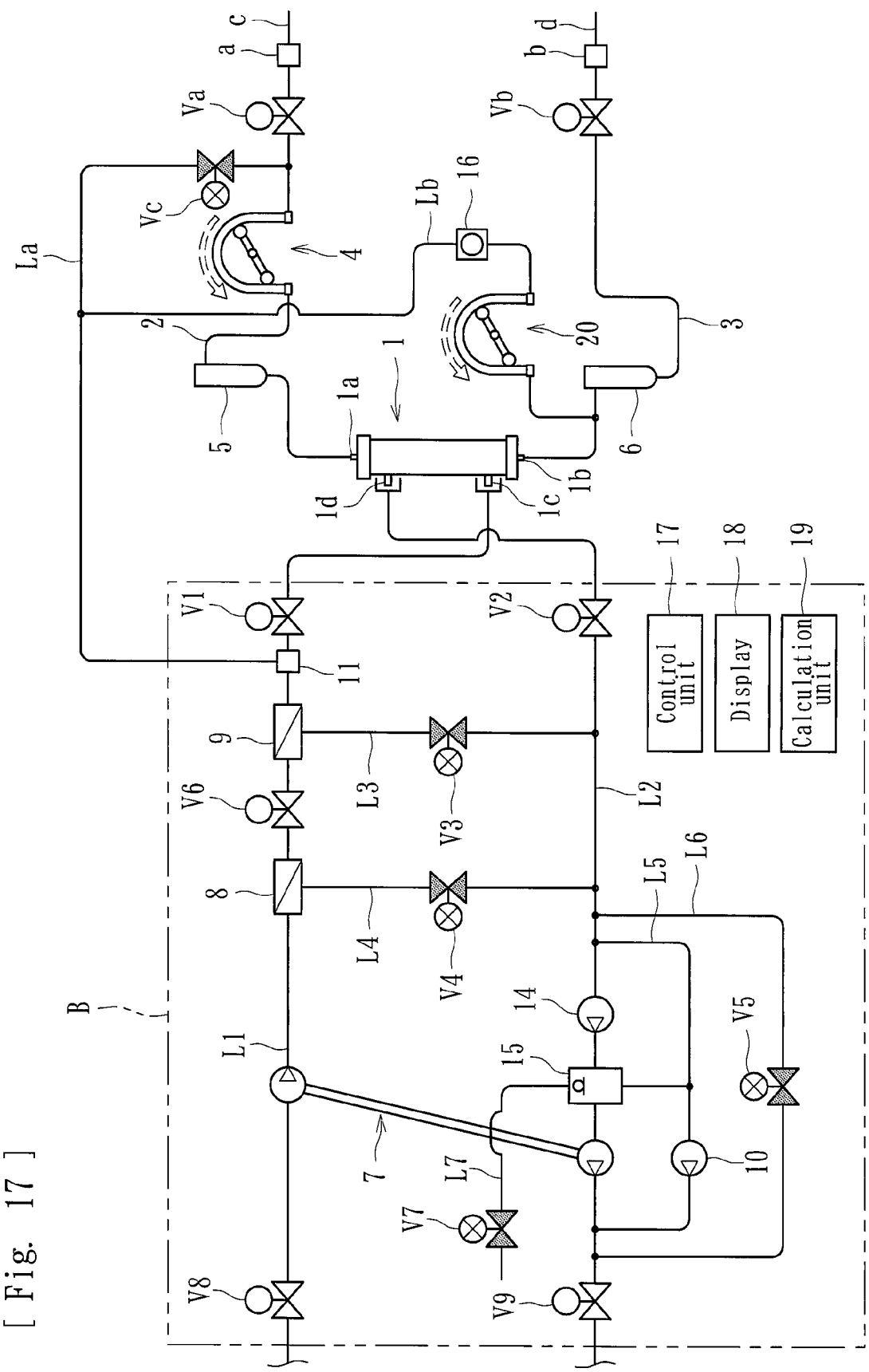
[Fig. 17]

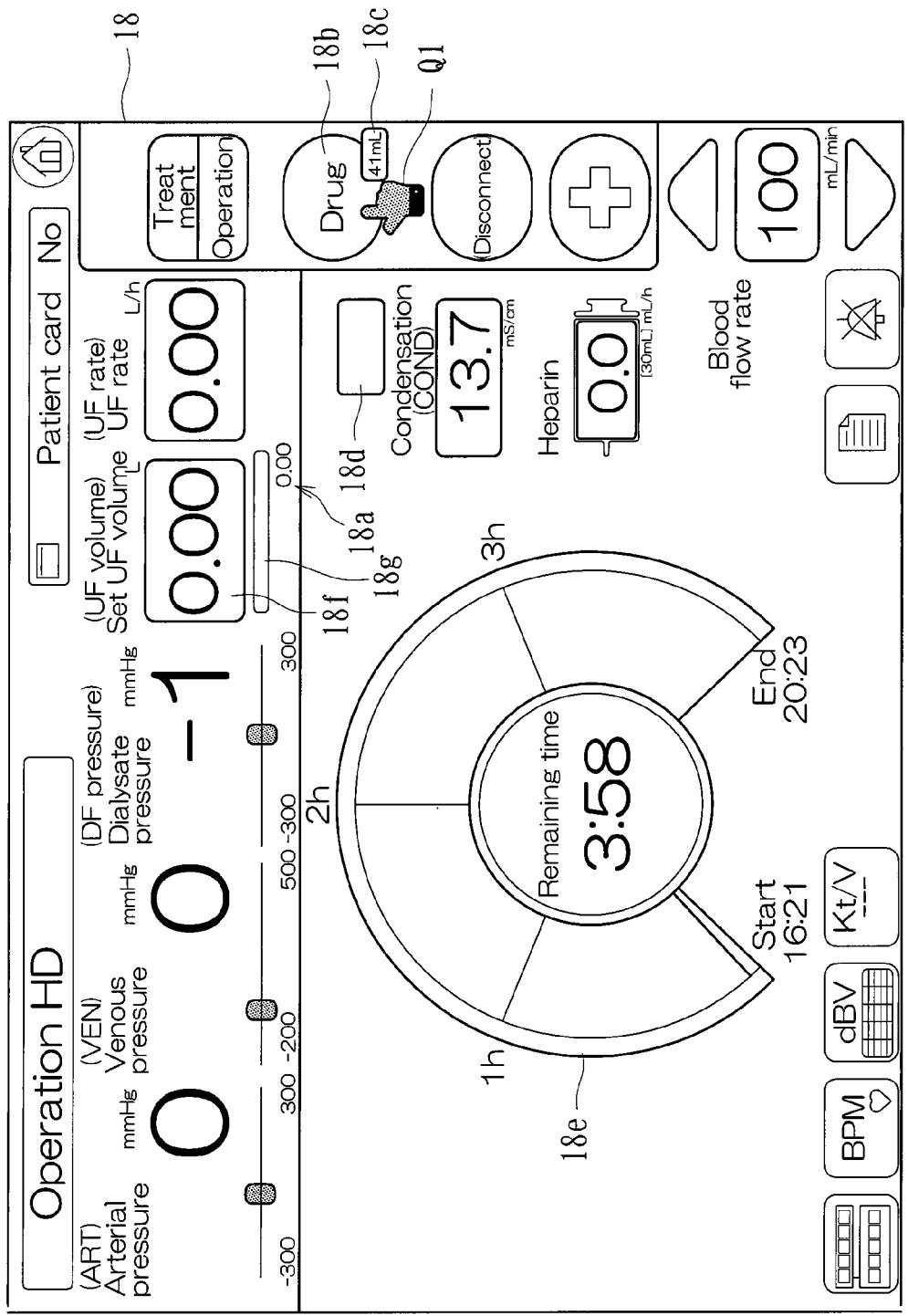
[Fig. 18]

[Fig. 19]
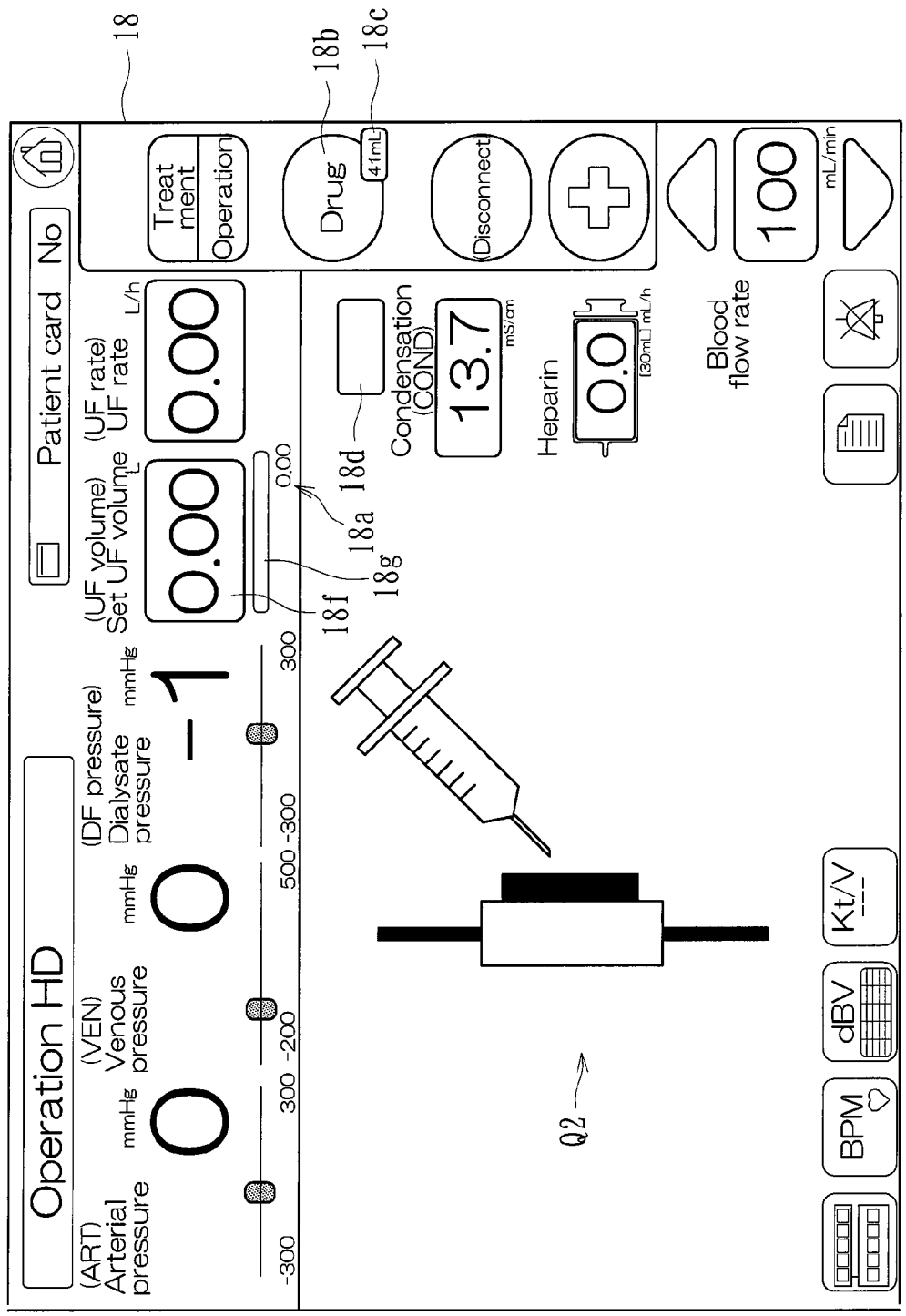

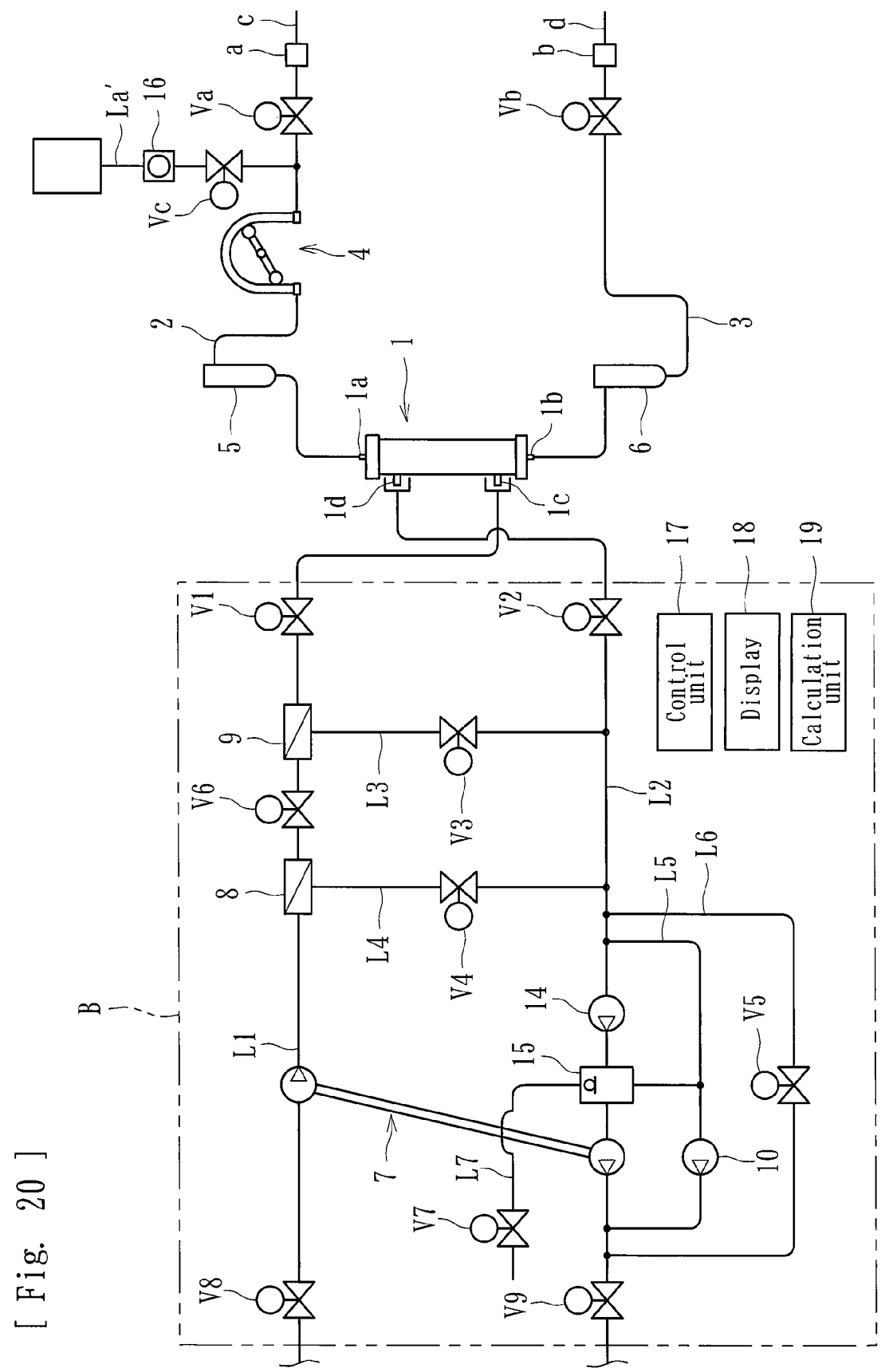
[Fig. 20]

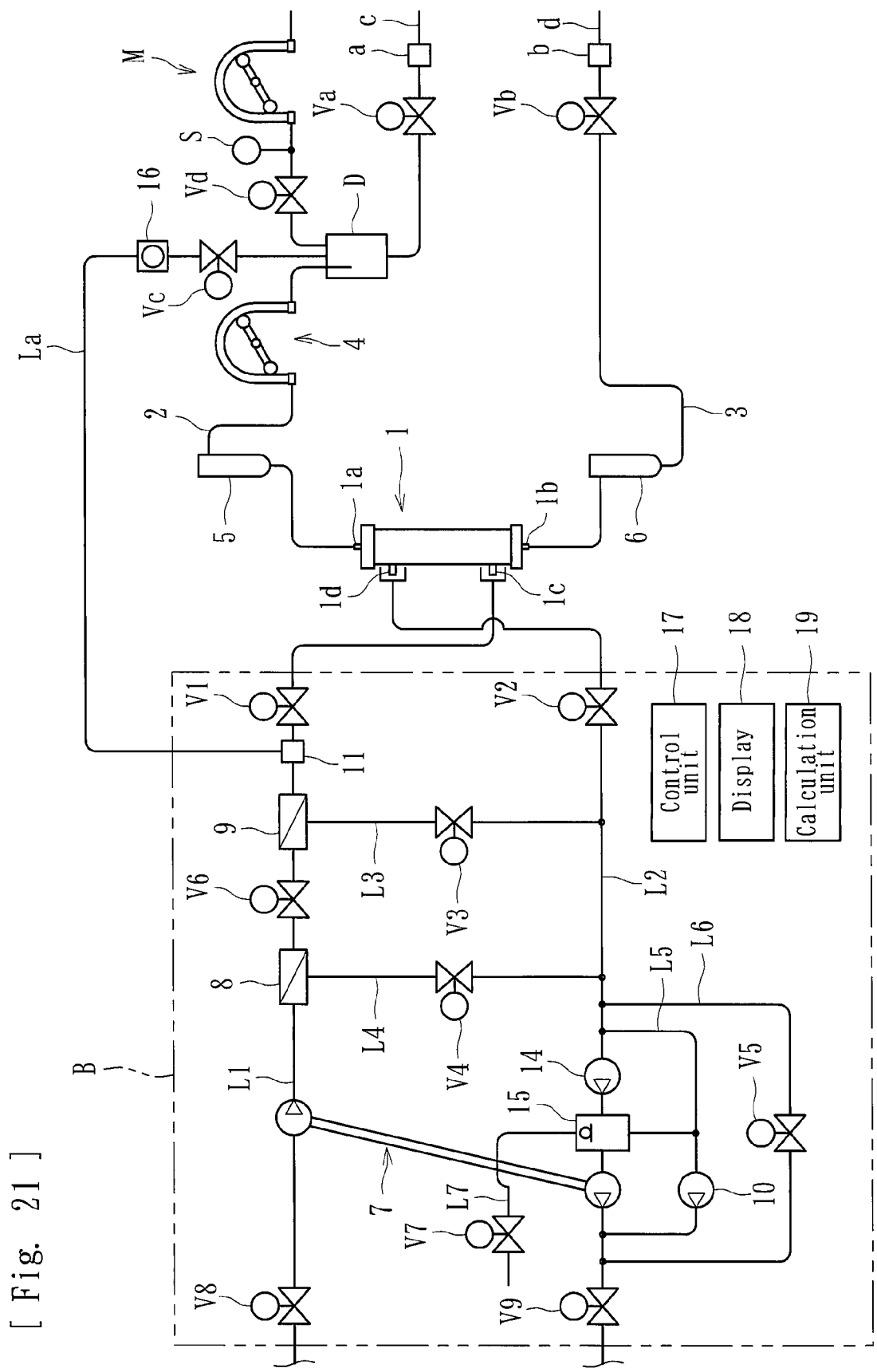
[Fig. 21]

BLOOD PURIFICATION APPARATUS

CROSS-REFERENCE TO RELATED APPLICATION(S)

This application is a continuation of International Application No. PCT/JP2020/018303 filed on Apr. 30, 2020, which claims priority to Japanese Application No. 2019-089299, filed on May 9, 2019, the entire disclosures of which are hereby incorporated by reference.

FIELD

The present teachings relate to a blood purification apparatus for giving blood purification treatment while causing blood of a patient to extracorporeally circulate.

BACKGROUND

In a technique of administering a liquid drug to a patient during a blood purification treatment that is performed by causing the patient's blood to extracorporeally circulate through a blood circuit, the liquid drug is infused into the blood circuit and is thus delivered into the patients body together with the patient's circulating blood returning into the patient's body. Regarding such a technique, there is a proposal for avoiding the direct infusion of a liquid drug into a blood circuit, in which the liquid drug is infused into a substitution line that allows a substitution fluid to be introduced into a blood line (see PTL 1, for example).

PTL 1: JP2013-506471 (a Published Japanese Translation of a PCT Application) the teachings of which are incorporated by reference herein for all purposes.

SUMMARY

However, in the above known technique of introducing the liquid drug into the blood circuit by infusing the liquid drug into the substitution line, since the blood is extracorporeally circulating through the blood circuit, some of the blood in the blood circuit may flow into the substitution line. If dialysate flowing in a dialysate introduction line is used as the substitution fluid to be introduced, the substitution line is normally closed unless the substitution fluid is being introduced into the blood circuit. Therefore, if the timing of infusion of the liquid drug is inappropriate, the infusion of the liquid drug may be inappropriate. Accordingly, there has been a demand for medical workers to be made aware of an appropriate timing of liquid drug infusion.

The present teachings have been conceived in view of the above circumstances and provides a blood purification apparatus in which blood flowing in a blood circuit is prevented from flowing into a substitution line when a liquid drug is infused from the substitution line into the blood circuit, and with which medical workers are made aware of an appropriate timing of liquid drug infusion.

According to variation 1, there is provided a blood purification apparatus that includes a blood circuit including an arterial blood circuit and a venous blood circuit and through which blood of a patient is allowed to extracorporeally circulate; a blood purification unit connected to and provided between the arterial blood circuit and the venous blood circuit and that purifies the blood flowing through the blood circuit; a blood pump provided to the arterial blood circuit and that delivers the blood of the patient from a distal end of the arterial blood circuit to a distal end of the venous blood circuit; a substitution line through which a substitution fluid is allowed to be introduced into the blood circuit; and an infusion portion attached to the substitution line and from which a predetermined liquid drug to be administered to the patient is allowed to be infused into the substitution line. The blood purification apparatus includes a control unit that executes a drug introduction mode in which the substitution fluid in the substitution line is introduced into the blood circuit, the control unit causing the liquid drug infused from the infusion portion in the drug introduction mode to be introduced into the blood circuit together with the substitution fluid; and a calculation unit that calculates a volume of the substitution fluid introduced from the substitution line into the blood circuit with the execution of the drug introduction mode.

According to variation 2, in the blood purification apparatus according to variation 1, a volume of water that corresponds to the volume of the substitution fluid calculated by the calculation unit is removed from the blood of the patient through the blood purification unit.

According to variation 3, in the blood purification apparatus according to variation 1 or 2, when the drug introduction mode is executed, the control unit controls a pressure at a connection between the blood circuit and the substitution line to be equal to or lower than a fluid pressure in the substitution line.

According to variation 4, the blood purification apparatus according to any of variations 1 to 3 further includes an arterial-blood-circuit opening-closing unit provided near a distal part of the arterial blood circuit and that is capable of arbitrarily opening or closing a liquid flow route; and a substitution-line opening-closing unit provided near a connection between the substitution line and the arterial blood circuit and that is capable of arbitrarily opening or closing a liquid flow route. Furthermore, the control unit executes the drug introduction mode by executing a negative-pressure-generating step of generating a negative pressure in a portion of the arterial blood circuit that is between the distal part and the blood pump by closing the substitution-line opening-closing unit and the arterial-blood-circuit opening-closing unit; a suction step of suctioning the substitution fluid in the substitution line into the arterial blood circuit by opening the substitution-line opening-closing unit after the negative-pressure-generating step; and an introduction step of introducing the substitution fluid in the substitution line into the arterial blood circuit by activating the blood pump after the suction step. Furthermore, the liquid drug infused from the infusion portion is suctioned or introduced into the blood circuit together with the substitution fluid in the suction step or the introduction step.

According to variation 5, in the blood purification apparatus according to any of variations 1 to 4, the control unit executes the drug introduction mode if a predetermined starting operation is performed.

According to variation 6, in the blood purification apparatus according to variation 4 or 5, the control unit causes the substitution fluid in the substitution line to be introduced into the arterial blood circuit by activating the blood pump in the suction step for the generation of the negative pressure and by keeping the blood pump active in the introduction step.

According to variation 7, the blood purification apparatus according to any of variations 4 to 6 further includes an air-trap chamber provided at the connection between the arterial blood circuit and the substitution line; and a liquid-level-adjusting pump that adjusts a surface level of a liquid layer in the air-trap chamber by introducing or discharging air into or from an air layer in the air-trap chamber. Furthermore, the control unit generates the negative pressure by activating the liquid-level-adjusting pump together with or instead of the blood pump in the suction step.

According to variation 8, the blood purification apparatus according to any of variations 1 to 3 further includes a substitution pump provided to the substitution line and that delivers the substitution fluid to the blood circuit. Furthermore, the control unit executes the drug introduction mode by executing an introduction step of introducing the substitution fluid in the substitution line into the blood circuit by activating the substitution pump. Furthermore, the liquid drug infused from the infusion portion is introduced into the blood circuit together with the substitution fluid in the introduction step.

According to variation 9, in the blood purification apparatus according to any of variations 1 to 8, a target ultrafiltration volume for water removal from the blood of the patient through the blood purification unit is settable. Furthermore, when the drug introduction mode is executed, the target ultrafiltration volume is corrected with an addition of the volume of the substitution fluid calculated by the calculation unit.

According to variation 10, the blood purification apparatus according to any of variations 1 to 9 further includes a dialysate introduction line through which dialysate is introduced into the blood purification unit; a drain-liquid discharge line into which drain liquid from the blood purification unit is discharged; and a bypass line connected to and communicating with the dialysate introduction line and the drain-liquid discharge line and through which the dialysate in the dialysate introduction line is allowed to bypass the blood purification unit and flow into the drain-liquid discharge line. Furthermore, the substitution line is connected to the dialysate introduction line and to the blood circuit in such a manner as to allow the dialysate in the dialysate introduction line to be introduced as the substitution fluid into the blood circuit. Furthermore, when the drug introduction mode is executed, the control unit executes a bypassing step in which the control unit causes the dialysate to flow through the bypass line by closing flow routes that allow the dialysate to be introduced into the blood purification unit through the dialysate introduction line and discharged from the blood purification unit into the drain-liquid discharge line.

According to variation 11, the blood purification apparatus according to any of variations 1 to 9 further includes a dialysate introduction line through which dialysate is introduced into the blood purification unit; and a drain-liquid discharge line into which drain liquid from the blood purification unit is discharged. Furthermore, the substitution line is connected to the dialysate introduction line and to the blood circuit in such a manner as to allow the dialysate in the dialysate introduction line to be introduced as the substitution fluid into the blood circuit. Furthermore, when the drug introduction mode is executed, the control unit causes a volume of water that corresponds to the volume of the substitution fluid introduced into the blood circuit to be removed through the blood purification unit.

According to variation 12, the blood purification apparatus according to variation 11 further includes a duplex pump provided astride the dialysate introduction line and the drain-liquid discharge line and that delivers the dialysate in the dialysate introduction line to the drain-liquid discharge line, the duplex pump equalizing a volume of the dialysate to be delivered through the dialysate introduction line and a volume of the drain liquid to be delivered through the drain-liquid discharge line.

According to variation 13, in the blood purification apparatus according to any of variations 1 to 12, an indication that prompts the execution of the drug introduction mode or an indication that prompts the infusion of the liquid drug from the infusion portion is displayed.

According to variation 14, in the blood purification apparatus according to any of variations 1 to 13, when the drug introduction mode is executed, the volume of the substitution fluid introduced from the substitution line into the blood circuit or a number of times of infusion of the liquid drug from the infusion portion is displayed.

According to variation 1, the blood purification apparatus includes the control unit that executes the drug introduction mode in which the substitution fluid in the substitution line is introduced into the blood circuit, the control unit causing the liquid drug infused from the infusion portion in the drug introduction mode to be introduced into the blood circuit together with the substitution fluid; and the calculation unit that calculates the volume of the substitution fluid introduced from the substitution line into the blood circuit with the execution of the drug introduction mode. Therefore, when a liquid drug is infused from the substitution line into the blood circuit, the blood flowing in the blood circuit is prevented from flowing into the substitution line. Furthermore, medical workers are made aware of an appropriate timing of liquid drug infusion.

According to variation 2, the volume of water that corresponds to the volume of the substitution fluid calculated by the calculation unit is removed from the blood of the patient through the blood purification unit. Therefore, the volume of water corresponding to the volume of the substitution fluid introduced into the patient's body together with the liquid drug is removed assuredly.

According to variation 3, when the drug introduction mode is executed, the control unit controls the pressure at the connection between the blood circuit and the substitution line to be equal to or lower than the fluid pressure in the substitution line. Therefore, the occurrence of backflow of the blood into the substitution line is avoided.

According to variation 4, the control unit executes the drug introduction mode by executing the negative-pressure-generating step of generating the negative pressure in the portion of the arterial blood circuit that is between the distal part and the blood pump by closing the substitution-line opening-closing unit and the arterial-blood-circuit opening-closing unit; the suction step of suctioning the substitution fluid in the substitution line into the arterial blood circuit by opening the substitution-line opening-closing unit after the negative-pressure-generating step; and the introduction step of introducing the substitution fluid in the substitution line into the arterial blood circuit by activating the blood pump after the suction step. Furthermore, the liquid drug infused from the infusion portion is suctioned or introduced into the blood circuit together with the substitution fluid in the suction step or the introduction step. Therefore, with the negative pressure thus generated, the blood flowing in the blood circuit is more assuredly prevented from flowing into the substitution line.

According to variation 5, the control unit executes the drug introduction mode if the predetermined starting operation is performed. Therefore, the liquid drug is infusible into the infusion portion with an arbitrary timing.

According to variation 6, the control unit causes the substitution fluid in the substitution line to be introduced into the arterial blood circuit by activating the blood pump in the suction step for the generation of the negative pressure and by keeping the blood pump active in the introduction step. Therefore, with the activation of the blood pump, the generation of the negative pressure in the negative-pressure-generating step and the introduction of the substitution fluid in the introduction step are achieved successively.

According to variation 7, the blood purification apparatus further includes the air-trap chamber provided at the connection between the arterial blood circuit and the substitution line; and the liquid-level-adjusting pump that adjusts the surface level of the liquid layer in the air-trap chamber by introducing or discharging air into or from the air layer in the air-trap chamber. Furthermore, the control unit generates the negative pressure by activating the liquid-level-adjusting pump together with or instead of the blood pump in the suction step. Therefore, the negative pressure to be generated in the negative-pressure-generating step is generated by utilizing the liquid-level-adjusting pump.

According to variation 8, the blood purification apparatus further includes the substitution pump provided to the substitution line and that delivers the substitution fluid to the blood circuit. Furthermore, the control unit executes the drug introduction mode by executing the introduction step of introducing the substitution fluid in the substitution line into the blood circuit by activating the substitution pump. Furthermore, the liquid drug infused from the infusion portion is introduced into the blood circuit together with the substitution fluid in the introduction step. Therefore, when the liquid drug is infused from the substitution line into the blood circuit, the activation of the substitution pump prevents the blood in the blood circuit from flowing into the substitution line. Furthermore, medical workers are made aware of an appropriate timing of liquid drug infusion.

According to variation 9, the target ultrafiltration volume for water removal from the blood of the patient through the blood purification unit is settable. Furthermore, when the drug introduction mode is executed, the target ultrafiltration volume is corrected with the addition of the volume of the substitution fluid calculated by the calculation unit. Therefore, the volume of water that corresponds to the volume of the substitution fluid introduced into the patient's body with the execution of the drug introduction mode is automatically removed in the blood purification treatment.

According to variation 10, the substitution line is connected to the dialysate introduction line and to the blood circuit in such a manner as to allow the dialysate in the dialysate introduction line to be introduced as the substitution fluid into the blood circuit. Furthermore, when the drug introduction mode is executed, the control unit executes the bypassing step in which the control unit causes the dialysate to flow through the bypass line by closing the flow routes that allow the dialysate to be introduced into the blood purification unit through the dialysate introduction line and discharged from the blood purification unit into the drain-liquid discharge line. Therefore, the liquid drug is prevented from being discharged from the blood purification unit into the drain-liquid discharge line.

According to variation 11, the substitution line is connected to the dialysate introduction line and to the blood circuit in such a manner as to allow the dialysate in the dialysate introduction line to be introduced as the substitution fluid into the blood circuit. Furthermore, when the drug introduction mode is executed, the control unit causes the volume of water that corresponds to the volume of the substitution fluid introduced into the blood circuit to be removed through the blood purification unit. Therefore, the volume of water that corresponds to the volume of the substitution fluid introduced into the blood circuit with the execution of the drug introduction mode is removed through the blood purification unit.

According to variation 12, the blood purification apparatus further includes the duplex pump provided astride the dialysate introduction line and the drain-liquid discharge line and that delivers the dialysate in the dialysate introduction line to the drain-liquid discharge line, the duplex pump equalizing the volume of the dialysate to be delivered through the dialysate introduction line and the volume of the drain liquid to be delivered through the drain-liquid discharge line. Therefore, when the duplex pump is activated, the volume of water that corresponds to the volume of the substitution fluid suctioned or introduced into the arterial blood circuit with the execution of the drug introduction mode is naturally removed through the blood purification unit.

According to variation 13, the indication that prompts the execution of the drug introduction mode or the indication that prompts the infusion of the liquid drug from the infusion portion is displayed. Therefore, medical workers are prevented from forgetting to start the drug introduction mode or to infuse the liquid drug from the infusion portion.

According to variation 14, when the drug introduction mode is executed, the volume of the substitution fluid introduced from the substitution line into the blood circuit or the number of times of infusion of the liquid drug from the infusion portion is displayed. Therefore, medical workers are correctly made aware of the volume of the substitution fluid or the number of times of infusion of the liquid drug.

BRIEF DESCRIPTION OF THE DRAWINGS

FIG. 1 is a schematic diagram of a blood purification apparatus according to an embodiment of the present teachings.

FIG. 2 is a schematic diagram illustrating items displayed on a display of the blood purification apparatus.

FIG. 3 is a flow chart illustrating a control sequence of a drug introduction mode executed in a blood purification apparatus according to a first embodiment of the present teachings.

FIG. 4 is a schematic diagram of the blood purification apparatus according to the first embodiment, illustrating a state during the treatment (a treatment mode).

FIG. 5 is a schematic diagram of the blood purification apparatus, illustrating a state at the transition to a bypassing step.

FIG. 6 is a schematic diagram of the blood purification apparatus, illustrating a state in a negative-pressure-generating step.

FIG. 7 is a schematic diagram of the blood purification apparatus, illustrating a state in a suction step and an introduction step.

FIG. 8 is a flow chart illustrating a control sequence of a drug introduction mode executed in a blood purification apparatus according to a second embodiment of the present teachings.

FIG. 9 is a flow chart illustrating a control sequence of a drug introduction mode executed in a blood purification apparatus according to a third embodiment of the present teachings.

FIG. 10 is a schematic diagram of the blood purification apparatus according to the third embodiment, illustrating a state in a negative-pressure-generating step.

FIG. 11 is a schematic diagram of the blood purification apparatus, illustrating a state in a suction step and an introduction step.

FIG. 12 is a flow chart illustrating a control sequence of a drug introduction mode executed in a blood purification apparatus according to a fourth embodiment of the present teachings.

FIG. 13 is a schematic diagram of the blood purification apparatus according to the fourth embodiment, illustrating a state during the treatment (a treatment mode).

FIG. 14 is a schematic diagram of the blood purification apparatus, illustrating a state at the transition to a bypassing step.

FIG. 15 is a schematic diagram of the blood purification apparatus, illustrating a state in an introduction step.

FIG. 16 is a flow chart illustrating a control sequence of a drug introduction mode executed in a blood purification apparatus according to a fifth embodiment of the present teachings.

FIG. 17 is a schematic diagram of the blood purification apparatus, illustrating a state in an introduction step.

FIG. 18 is a schematic diagram illustrating items (an indication that prompts the execution of the drug introduction mode) provided on a display of a blood purification apparatus according to another embodiment of the present teachings.

FIG. 19 is a schematic diagram illustrating items (an indication that prompts the infusion of a liquid drug from an infusion portion) provided on a display of a blood purification apparatus according to yet another embodiment of the present teachings.

FIG. 20 is a schematic diagram of a blood purification apparatus according to yet another embodiment of the present teachings (in which a substitution fluid is supplied from a substitution-fluid bag).

FIG. 21 is a schematic diagram of a blood purification apparatus according to yet another embodiment of the present teachings (that includes a liquid-level-adjusting pump).

DETAILED DESCRIPTION

Embodiments of the present teachings will now be described specifically with reference to the drawings.

A blood purification apparatus according to each of the following embodiments is applied to a hemodialysis apparatus and basically includes, as illustrated in FIG. 1, a blood circuit in which an arterial blood circuit 2 and a venous blood circuit 3 are connected to a dialyzer 1, which serves as a blood purification unit; a dialysis device B including a duplex pump 7, an ultrafiltration pump 10, a dialysate introduction line L1, and a drain-liquid discharge line L2; a substitution line La provided with an infusion portion 16; a control unit 17; a display 18; and a calculation unit 19.

The dialyzer 1 has thereinside blood purification membranes, which are not illustrated (while the present embodiment employs hollow-fiber hemodialysis membranes or hemodiafiltration membranes, flat hemodialysis membranes may be employed). The dialyzer 1 further has a blood inlet 1a, through which blood is introduced thereinto; a blood outlet 1b, through which the blood introduced thereinto is discharged therefrom; a dialysate inlet 1c, through which dialysate is introduced thereinto; and a dialysate outlet 1d, through which the dialysate introduced thereinto is discharged therefrom. The blood introduced into the dialyzer 1 through the blood inlet 1a comes into contact with the dialysate through the hollow fiber membranes, thereby being purified.

The arterial blood circuit 2 basically includes a flexible tube. One end of the arterial blood circuit 2 is connected to the blood inlet 1a of the dialyzer 1, whereby the blood collected from a blood vessel of the patient is introduced into the hollow fiber membranes provided in the dialyzer 1. The other end of the arterial blood circuit 2 is provided with a connector a, to which an arterial puncture needle c is attachable. The arterial blood circuit 2 is further provided at halfway positions thereof with an arterial air-trap chamber 5 for bubble removal and a blood pump 4.

The blood pump 4 is a peristaltic pump provided to the arterial blood circuit 2. When the blood pump 4 is activated, the blood pump 4 squeezes the flexible tube to cause the patient's blood to flow from the side of the arterial puncture needle c toward the blood inlet 1a of the dialyzer 1. With the activation of the blood pump 4, the patient's blood is caused to extracorporeally circulate from the distal end of the arterial blood circuit 2 to the distal end of the venous blood circuit 3.

As with the arterial blood circuit 2, the venous blood circuit 3 basically includes a flexible tube. One end of the venous blood circuit 3 is connected to the blood outlet 1b of the dialyzer 1, whereby the blood having flowed through the hollow fiber membranes is discharged from the dialyzer 1. The other end of the venous blood circuit 3 is provided with a connector b, to which a venous puncture needle d is attachable. The venous blood circuit 3 is further provided at a halfway position thereof with a venous air-trap chamber 6 for bubble removal. The patient's blood collected through the arterial puncture needle c flows through the arterial blood circuit 2 and reaches the dialyzer 1, where the blood is purified. Then, the blood flows through the venous blood circuit 3 and returns into the patient's body through the venous puncture needle d. Thus, the extracorporeal circulation of the blood is achieved. In this specification, the side on which the puncture needle for blood removal (blood collection) is provided is referred to as the "arterial" side, and the side on which the puncture needle for blood return is provided is referred to as the "venous" side. The "arterial" side and the "venous" side are not defined in accordance with which of the artery and the vein is to be the object of puncture.

The arterial blood circuit 2 is further provided with a clamp unit Va (an arterial-blood-circuit opening-closing unit) at a position near the distal end thereof (a position between the connector a and the blood pump 4 and near the connector a). The clamp unit Va is capable of opening or closing the flow route. The venous blood circuit 3 is further provided with a clamp unit Vb at a position near the distal end thereof (a position between the connector b and the venous air-trap chamber 6 and near the connector b). The clamp unit Vb is capable of opening or closing the flow route. The clamp unit Va is provided near a distal part of the arterial blood circuit 2 and serves as an "arterial-blood-circuit opening-closing unit", which is capable of arbitrarily opening or closing the liquid flow route.

The dialysate inlet 1c and the dialysate outlet 1d of the dialyzer 1 receive an end of the dialysate introduction line L1 and an end of the drain-liquid discharge line L2 connected thereto, respectively. The dialysate introduced into the dialyzer 1 through the dialysate introduction line L1 flows through spaces outside the hollow fiber membranes and is discharged as drain liquid into the drain-liquid discharge line L2. The spaces inside the hollow fiber membranes (purification membranes) provided in the dialyzer 1 serve as blood flow routes through which the blood is allowed to flow. The spaces outside the hollow fiber membranes serve as dialysate flow routes through which the dialysate is allowed to flow.

The dialysis device B, which includes the dialysate introduction line L1 and the drain-liquid discharge line L2, further includes the duplex pump 7, bypass lines L3 to L6, and electromagnetic valves V1 to V9. The duplex pump 7 is provided astride the dialysate introduction line L1 and the drain-liquid discharge line L2. The duplex pump 7 causes the dialysate, which is prepared to have a predetermined condensation in advance, to be introduced into the dialyzer 1 and also causes the dialysate used for dialysis to be discharged from the dialyzer 1.

The duplex pump 7 according to the present embodiment includes a pump chamber on the supply side and a pump chamber on the drain side that have equal capacities, so that the volume of the dialysate to be delivered through the dialysate introduction line L1 and the volume of the drain liquid to be delivered through the drain-liquid discharge line L2 become equal. The duplex pump 7 may be replaced with a delivery unit of another type (not limited to a pump and may be a balance chamber or the like) that is capable of delivering the dialysate in the dialysate introduction line L1 to the dialyzer 1.

The dialysate introduction line L1 is provided with the electromagnetic valve V1 at a halfway position thereof (a position on the downstream side (nearer to the dialyzer 1) with respect to the joint between the dialysate introduction line L1 and the substitution line La). The drain-liquid discharge line L2 is provided with the electromagnetic valve V2 at a halfway position thereof (a position on the upstream side (nearer to the dialyzer 1) with respect to the joint between the drain-liquid discharge line L2 and the bypass line L3). The dialysate introduction line L1 is further provided with filters 8 and 9 at respective positions between the duplex pump 7 and the electromagnetic valve V1. The filters 8 and 9 filter and thus purify the dialysate flowing through the dialysate introduction line L1 and are connected to the bypass lines L3 and L4, respectively. The bypass lines L3 and L4 each serve as a bypass to the drain-liquid discharge line L2 so as to introduce the dialysate into the drain-liquid discharge line L2.

The bypass lines L3 and L4 are provided with the electromagnetic valves V3 and V4, respectively. When the electromagnetic valve V3 or the electromagnetic valve V4 is opened to open the corresponding flow route, the dialysate in the dialysate introduction line L1 is allowed to bypass the dialyzer 1 and flow into the drain-liquid discharge line L2. The dialysate introduction line L1 is further provided with the electromagnetic valve V6 at a position between the filter 8 and the filter 9.

The drain-liquid discharge line L2 is provided with the bypass lines L5 and L6. The bypass lines L5 and L6 each bypass the drain side of the duplex pump 7. The bypass line L5 is provided with the ultrafiltration pump 10, which is provided for removing water from the patient's blood flowing through the dialyzer 1. The bypass line L6 is provided with the electromagnetic valve V5, which is capable of opening or closing the flow route.

The drain-liquid discharge line L2 is further provided with a pressurizing pump 14 at a position on the upstream side with respect to the duplex pump 7 (between a joint to the bypass line L5 and the duplex pump 7). The pressurizing pump 14 adjusts the fluid pressure on the drain side of the duplex pump 7. The drain-liquid discharge line L2 is further provided with a degassing chamber 15 at a position on the upstream side with respect to the duplex pump 7 (between the pressurizing pump 14 and the duplex pump 7). The degassing chamber 15 is provided with an atmosphere release line L7 connected thereto through a check valve or the like. The atmosphere release line L7 is provided with the electromagnetic valve V7.

The substitution line La is connected to the arterial blood circuit 2 at a position between the distal part and the blood pump 4, whereby a substitution fluid is allowed to be introduced into the arterial blood circuit 2. More specifically, one end of the substitution line La according to the present embodiment is connected to a collecting port 11 (a so-called sampling port), which is provided to the dialysate introduction line L1. The other end of the substitution line La is connected to the arterial blood circuit 2. The substitution line La serves as a flow route through which the dialysate in the dialysate introduction line L1 is allowed to be supplied to the arterial blood circuit 2.

The substitution line La is provided with a clamp unit Vc, which is capable of opening or closing the flow route. When the clamp unit Vc is open, the dialysate is supplied to the blood circuit through the dialysate introduction line L1, whereby priming to be performed before the treatment, substitution (emergency fluid infusion) to be performed during the treatment, or blood return to be performed after the treatment is enabled. The clamp unit Vc is provided near the connection between the substitution line La and the arterial blood circuit 2 and serves as a "substitution-line opening-closing unit", which is capable of arbitrarily opening or closing the liquid flow route.

The substitution line La according to the present embodiment is further provided with a rubber button 16 (an infusion portion) at a position between the collecting port 11 and the clamp unit Vc. The rubber button 16 allows a predetermined liquid drug (such as EPO (erythropoietin) (an erythropoiesis stimulating agent), or the like) that should be administered to the patient to be infused into the substitution line La. For example, the distal end of a syringe or the like is stuck into the rubber button 16, and the predetermined liquid drug is infused. The rubber button 16 may be replaced with an infusion portion of another type that allows the infusion of the predetermined liquid drug.

The control unit 17 is, for example, a microcomputer or the like provided in the dialysis device B and controls at least the following: operations of opening or closing the actuators such as the blood pump 4 and the duplex pump 7, the electromagnetic valves V1 to V9, and the clamp units (Va to Vd) (particularly the clamp unit Va serving as the arterial-blood-circuit opening-closing unit and the clamp unit Vc serving as the substitution-line opening-closing unit). The control unit 17 is electrically connected to sensors such as fluid-pressure measurement sensors, a venous-pressure sensor, bubble detection sensors, condensation sensors, temperature sensors (all not illustrated) so as to be able to execute predetermined control sequences.

In the present embodiment, substitution (emergency fluid infusion) to be performed during the treatment and blood return to be performed after the treatment are achievable by supplying the dialysate in the dialysate introduction line L1 to the blood circuit. Emergency fluid infusion is a step of supplying the dialysate, serving as an emergency fluid, to the blood circuit if, for example, the blood pressure of the patient drops excessively during the treatment. Blood return is a step of returning the blood remaining in the blood circuit to the patient by supplying the dialysate, serving as the substitution fluid, to the blood circuit after the treatment.

The control unit 17 according to the present embodiment executes a drug introduction mode, which includes a negative-pressure-generating step (a pressure-controlling step) of generating a negative pressure in a portion of the arterial blood circuit 2 that is between the distal part and the blood pump 4 by closing the clamp unit Vc (the substitution-line opening-closing unit) and the clamp unit Va (the arterial-blood-circuit opening-closing unit); a suction step of suctioning the substitution fluid in the substitution line La into the arterial blood circuit 2 by opening the clamp unit Vc after the negative-pressure-generating step (the pressure-controlling step); and an introduction step of introducing the substitution fluid in the substitution line La into the arterial blood circuit 2 by activating the blood pump 4 after the suction step. In the suction step or the introduction step, the liquid drug infused from the rubber button 16 (the infusion portion) is suctioned or introduced into the arterial blood circuit 2 together with the substitution fluid.

The display 18 is a touch panel attached to the dialysis device B and is capable of displaying the following, as illustrated in FIG. 2: a target-ultrafiltration-volume display portion 18a, in which a target ultrafiltration volume is displayed; a starting portion 18b, which enables an operation of starting the drug introduction mode; a substitution-volume display portion 18c, in which the volume of the substitution fluid introduced from the substitution line La into the arterial blood circuit 2 with the execution of the drug introduction mode is displayed; a number-of-executions display portion 18d, in which the number of times of execution of the drug introduction mode (that is, the number of times of infusion of the liquid drug from the rubber button 16 (the infusion portion)) is displayed; a treatment display portion 18e, in which the duration and the like of the blood purification treatment are displayed; an actual-measurement display portion 18f, in which the ultrafiltration volume (the actual ultrafiltration volume) measured in the blood purification treatment (the treatment mode) is displayed; and a ratio display portion 18g, in which the ratio of the actual ultrafiltration volume to the target ultrafiltration volume is displayed in the form of a gauge.

When a medical worker touches the starting portion 18b (a predetermined operation), the drug introduction mode is executed by the control unit 17, in which the volume of the substitution fluid introduced from the substitution line La into the arterial blood circuit 2 with the execution of the drug introduction mode is displayed in the substitution-volume display portion 18c, and the number of times of infusion of the liquid drug from the rubber button 16 in the current blood purification treatment is displayed in the number-of-executions display portion 18d. The calculation unit 19 calculates the volume of the substitution fluid introduced from the substitution line La into the arterial blood circuit 2 with the execution of the drug introduction mode. The volume of the substitution fluid thus calculated is displayed in the substitution-volume display portion 18c.

The display 18 may further provide an indication Q1, illustrated in FIG. 18, which prompts the execution of the drug introduction mode; or an indication Q2, illustrated in FIG. 19, which prompts the infusion of the liquid drug from the rubber button 16 (the infusion portion). For example, when the drug introduction mode is expected to be started, the indication Q1 is preferably provided as an image of a hand pointing the starting portion 18b (see FIG. 18). On the other hand, when the infusion of the liquid drug is expected to be performed, the indication provided in the treatment display portion 18e is preferably changed to the indication Q2, which is an image of a syringe and the rubber button 16 (see FIG. 19).

Now, a control sequence, executed by the control unit 17, according to a first embodiment will be described with reference to the flow chart illustrated in FIG. 3.

In the blood purification treatment, as illustrated in FIG. 4, when the blood pump 4 and the duplex pump 7 are activated while a patient is punctured with the arterial puncture needle c and the venous puncture needle d, the patient's blood is caused to extracorporeally circulate through the arterial blood circuit 2 and the venous blood circuit 3, whereby the blood undergoes the blood purification treatment in the dialyzer 1. In the blood purification treatment (the treatment mode), as illustrated in FIG. 4, the clamp unit Va (the arterial-blood-circuit opening-closing unit) and the clamp unit Vb are open, whereas the clamp unit Vc (the substitution-line opening-closing unit) and the electromagnetic valves V3 and V4 are closed.

If a liquid drug needs to be administered to the patient in, for example, the middle or last phase of the blood purification treatment, a medical worker touches the starting portion 18b of the display 18, whereby the drug introduction mode is executed. When the drug introduction mode is executed, as illustrated in FIG. 5, the blood pump 4 is temporarily stopped. Furthermore, the electromagnetic valves V1 and V2 are closed. Furthermore, with the electromagnetic valve V4 kept closed, the electromagnetic valve V3 is opened, whereby the control sequence proceeds to a bypassing step S1.

In the bypassing step S1, the flow routes that allow the dialysate to be introduced into the dialyzer 1 (the blood purification unit) through the dialysate introduction line L1 and discharged from the dialyzer 1 (the blood purification unit) into the drain-liquid discharge line L2 are closed (that is, the electromagnetic valves V1 and V2 are closed), whereby the dialysate is caused to flow through the bypass line L3. When the bypassing step S1 ends and the introduction of the dialysate into the dialyzer 1 and the discharge of the drain liquid from the dialyzer 1 are stopped, the negative-pressure-generating step (the pressure-controlling step) S2 is executed.

In the negative-pressure-generating step (the pressure-controlling step) S2, as illustrated in FIG. 6, the blood pump 4 is activated with the clamp unit Vc (the substitution-line opening-closing unit) and the clamp unit Va (the arterial-blood-circuit opening-closing unit) closed, whereby a negative pressure is generated in a portion of the arterial blood circuit 2 that is between the distal part (the part closed by the clamp unit Va) and the blood pump 4. Specifically, since the clamp unit Va and the clamp unit Vc are closed, a closed circuit is established, in which the blood pump 4 is activated. Accordingly, the blood in the closed circuit is discharged toward the downstream side with respect to the blood pump 4. Consequently, a negative pressure is generated. The negative-pressure-generating step (the pressure-controlling step) S2 is continued until the number of revolutions of the rotor of the blood pump 4 reaches a preset value or until a predetermined period of time elapses after the start of the activation of the blood pump 4. When the negative-pressure-generating step (the pressure-controlling step) S2 ends, the suction step S3 is executed.

In the suction step S3 subsequent to the negative-pressure-generating step (the pressure-controlling step) S2, as illustrated in FIG. 7, the blood pump 4 is kept active, and the clamp unit Vc (the substitution-line opening-closing unit) is opened, whereby the substitution fluid in the substitution line La is suctioned into the arterial blood circuit 2. Specifically, in the negative-pressure-generating step (the pressure-controlling step) S2, a negative pressure is generated at the connection between the arterial blood circuit 2 and the substitution line La. In such a state, when the clamp unit Vc is opened, the substitution fluid in the substitution line La is suctioned under the negative pressure into the arterial blood circuit 2. The suction step S3 is continued until the number of revolutions of the rotor of the blood pump 4 reaches a preset value or until a predetermined period of time elapses after the start of the suction step S3. When the suction step S3 ends, the introduction step S4 is executed.

In the introduction step S4 subsequent to the suction step S3, as illustrated in FIG. 7, the blood pump 4 is kept active, the clamp unit Vc (the substitution-line opening-closing unit) is kept open, and the clamp unit Va (the arterial-blood-circuit opening-closing unit) is kept closed, whereby the blood pump 4 that is active causes the substitution fluid in the substitution line La to be introduced into the arterial blood circuit 2. Specifically, when the suction step S3 ends, the negative pressure at the connection between the arterial blood circuit 2 and the substitution line La is removed. Therefore, with the blood pump 4 kept active for liquid delivery, the substitution fluid in the substitution line La is introduced into the arterial blood circuit 2.

Accordingly, if a liquid drug to be administered to the patient is infused from the rubber button 16 during a period between the suction step S3 and the introduction step S4 inclusive, the liquid drug thus infused is suctioned or introduced into the arterial blood circuit 2 together with the substitution fluid in the substitution line La. Meanwhile, on the display 18, the volume of the substitution fluid introduced into the arterial blood circuit 2 with the execution of the drug introduction mode is displayed in the substitution-volume display portion 18c, and the number of times of execution of the drug introduction mode is displayed in the number-of-executions display portion 18d. The timing of infusion of the liquid drug from the rubber button 16 is arbitrary but is preferably a point between the suction step S3 and the introduction step S4 inclusive.

Then, in S5, it is determined whether or not a preset volume of the substitution fluid (the substitution fluid containing the liquid drug) has been introduced from the substitution line La into the arterial blood circuit 2 in the introduction step S4. If it is determined that the preset volume of the substitution fluid has been introduced, the sequence proceeds to S6, where the mode is changed to the treatment mode illustrated in FIG. 4. Thus, the sequence of the drug introduction mode ends, and the mode is changed to the treatment mode to restart the blood purification treatment. In the blood purification treatment, the driving speed of the blood pump 4 before the execution of the drug introduction mode is stored. After the drug introduction mode is complete, the stored driving speed is resumed.

Now, a control sequence, executed by the control unit 17, according to a second embodiment will be described with reference to the flow chart illustrated in FIG. 8.

The present embodiment employs the same steps S1 to S5 as those employed by the first embodiment. In S5, it is determined whether or not a preset volume of the substitution fluid (the substitution fluid containing the liquid drug) has been introduced from the substitution line La into the arterial blood circuit 2 in the introduction step S4. If it is determined that the preset volume of the substitution fluid has been introduced, the sequence proceeds to S6, where the target ultrafiltration volume is corrected.

To summarize, in the present embodiment, a target ultrafiltration volume for water removal from the patient's blood through the dialyzer 1 is settable. Furthermore, the calculation unit 19 calculates the volume of the substitution fluid introduced from the substitution line La into the arterial blood circuit 2 with the execution of the drug introduction mode. Therefore, when the drug introduction mode is executed, the target ultrafiltration volume is corrected with the addition of the volume of the substitution fluid calculated by the calculation unit 19.

After the target ultrafiltration volume is corrected as above, the sequence proceeds to S7, where the mode is changed to the treatment mode illustrated in FIG. 4. Thus, the sequence of the drug introduction mode ends, and the mode is changed to the treatment mode to restart the blood purification treatment. In the blood purification treatment, as with the case of the first embodiment, the driving speed of the blood pump 4 before the execution of the drug introduction mode is stored. After the drug introduction mode is complete, the stored driving speed is resumed.

Now, a control sequence, executed by the control unit 17, according to a third embodiment will be described with reference to the flow chart illustrated in FIG. 9.

In the blood purification treatment, as with the case of the first embodiment and as illustrated in FIG. 4, when the blood pump 4 and the duplex pump 7 are activated while a patient is punctured with the arterial puncture needle c and the venous puncture needle d, the patient's blood is caused to extracorporeally circulate through the arterial blood circuit 2 and the venous blood circuit 3, whereby the blood undergoes the blood purification treatment in the dialyzer 1. In the blood purification treatment (the treatment mode), as illustrated in FIG. 4, the clamp unit Va (the arterial-blood-circuit opening-closing unit) and the clamp unit Vb are open, whereas the clamp unit Vc (the substitution-line opening-closing unit) and the electromagnetic valves V3 and V4 are closed.

If a liquid drug needs to be administered to the patient in, for example, the middle or last phase of the blood purification treatment, a medical worker touches the starting portion 18b of the display 18, whereby the drug introduction mode is executed. When the drug introduction mode is executed, the blood pump 4 is temporarily stopped (see FIG. 5). Then, as illustrated in FIG. 10, the clamp unit Va (the arterial-blood-circuit opening-closing unit) and the clamp unit Vc (the substitution-line opening-closing unit) are closed.

In this state, the electromagnetic valves V3 and V4 are closed, the electromagnetic valves V1 and V2 are open, and the duplex pump 7 is active. Therefore, the dialysate is introduced into the dialyzer 1 through the dialysate introduction line L1, and the resulting drain liquid is discharged from the dialyzer 1 into the drain-liquid discharge line L2. Furthermore, since the duplex pump 7 is active, the volume of the dialysate delivered through the dialysate introduction line L1 and the volume of the drain liquid delivered through the drain-liquid discharge line L2 are equal. Subsequently, the blood pump 4 is activated, whereby the negative-pressure-generating step (the pressure-controlling step) S1 is executed.

In the negative-pressure-generating step (the pressure-controlling step) S1, as illustrated in FIG. 10, the blood pump 4 is activated with the clamp unit Vc (the substitution-line opening-closing unit) and the clamp unit Va (the arterial-blood-circuit opening-closing unit) closed, whereby a negative pressure is generated in a portion of the arterial blood circuit 2 that is between the distal part (the part closed by the clamp unit Va) and the blood pump 4. Specifically, since the clamp unit Va and the clamp unit Vc are closed, a closed circuit is established, in which the blood pump 4 is activated. Accordingly, the blood in the closed circuit is discharged toward the downstream side with respect to the blood pump 4. Consequently, a negative pressure is generated. The negative-pressure-generating step (the pressure-controlling step) S1 is continued until the number of revolutions of the rotor of the blood pump 4 reaches a preset value or until a predetermined period of time elapses after the start of the activation of the blood pump 4. When the negative-pressure-generating step (the pressure-controlling step) S1 ends, the suction step S2 is executed.

In the suction step S2 subsequent to the negative-pressure-generating step (the pressure-controlling step) S1, as illustrated in FIG. 11, the blood pump 4 is kept active, and the clamp unit Vc (the substitution-line opening-closing unit) is opened, whereby the substitution fluid in the substitution line La is suctioned into the arterial blood circuit 2. Specifically, in the negative-pressure-generating step (the pressure-controlling step) S1, a negative pressure is generated at the connection between the arterial blood circuit 2 and the substitution line La. In such a state, when the clamp unit Vc is opened, the substitution fluid in the substitution line La is suctioned under the negative pressure into the arterial blood circuit 2. The suction step S2 is continued until the number of revolutions of the rotor of the blood pump 4 reaches a preset value or until a predetermined period of time elapses after the start of the suction step S2. When the suction step S2 ends, the introduction step S3 is executed.

In the introduction step S3 subsequent to the suction step S2, as illustrated in FIG. 11, the blood pump 4 is kept active, the clamp unit Vc (the substitution-line opening-closing unit) is kept open, and the clamp unit Va (the arterial-blood-circuit opening-closing unit) is kept closed, whereby the blood pump 4 that is active causes the substitution fluid in the substitution line La to be introduced into the arterial blood circuit 2. Specifically, when the suction step S2 ends, the negative pressure at the connection between the arterial blood circuit 2 and the substitution line La is removed. Therefore, with the blood pump 4 kept active for liquid delivery, the substitution fluid in the substitution line La is introduced into the arterial blood circuit 2.

Accordingly, if a liquid drug to be administered to the patient is infused from the rubber button 16 during a period between the suction step S2 and the introduction step S3 inclusive, the liquid drug thus infused is suctioned or introduced into the arterial blood circuit 2 together with the substitution fluid in the substitution line La. Meanwhile, on the display 18, the volume of the substitution fluid introduced into the arterial blood circuit 2 with the execution of the drug introduction mode is displayed in the substitution-volume display portion 18c, and the number of times of execution of the drug introduction mode is displayed in the number-of-executions display portion 18d.

In the present embodiment, since the duplex pump 7 is active, the volume of the dialysate delivered through the dialysate introduction line L1 and the volume of the drain liquid delivered through the drain-liquid discharge line L2 are equal. Therefore, when the drug introduction mode is executed, a volume of water that corresponds to the volume of the substitution fluid introduced into the arterial blood circuit 2 in the suction step S2 or the introduction step S3 is removed through the dialyzer 1.

Specifically, when the clamp unit Vc is open, some of the dialysate in the dialysate introduction line L1 flows into the substitution line La and reaches the arterial blood circuit 2. Therefore, the volume of the dialysate introduced into the dialyzer 1 becomes smaller than the volume of the drain liquid by the volume of the dialysate flowing into the substitution line La. Consequently, a volume of water corresponding to the reduction is discharged from the dialyzer 1 into the drain-liquid discharge line L2. Therefore, when the drug introduction mode is executed, the volume of water that corresponds to the volume of the substitution fluid introduced into the arterial blood circuit 2 in the suction step S2 or the introduction step S3 is naturally removed through the dialyzer 1.

Then, in S4, it is determined whether or not a preset volume of the substitution fluid (the substitution fluid containing the liquid drug) has been introduced from the substitution line La into the arterial blood circuit 2 in the introduction step S3. If it is determined that the preset volume of the substitution fluid has been introduced, the sequence proceeds to S5, where the mode is changed to the treatment mode illustrated in FIG. 4. Thus, the sequence of the drug introduction mode ends, and the mode is changed to the treatment mode to restart the blood purification treatment. In the blood purification treatment, the driving speed of the blood pump 4 before the execution of the drug introduction mode is stored. After the drug introduction mode is complete, the stored driving speed is resumed.

Now, a control sequence, executed by the control unit 17, according to a fourth embodiment will be described with reference to the flow chart illustrated in FIG. 12.

In the blood purification treatment, as illustrated in FIG. 13, when the blood pump 4 and the duplex pump 7 are activated while a patient is punctured with the arterial puncture needle c and the venous puncture needle d, the patient's blood is caused to extracorporeally circulate through the arterial blood circuit 2 and the venous blood circuit 3, whereby the blood undergoes the blood purification treatment in the dialyzer 1. In the blood purification treatment (the treatment mode), as illustrated in FIG. 13, the clamp unit Va (the arterial-blood-circuit opening-closing unit) and the clamp unit Vb are open, whereas the clamp unit Vc (the substitution-line opening-closing unit) and the electromagnetic valves V3 and V4 are closed.

The blood purification apparatus according to the present embodiment includes a substitution line Lb branching off from a halfway position of the substitution line La and connected to a position of the venous blood circuit 3 that is between the dialyzer 1 and the venous air-trap chamber 6. The apparatus further includes a substitution pump 20 provided to the substitution line Lb. When the substitution pump 20 is activated, the dialysate serving as the substitution fluid is introduced from the dialysate introduction line L1 into the venous blood circuit 3. The substitution pump 20 is a peristaltic pump. When the substitution pump 20 is activated, the substitution pump 20 squeezes the flexible tube to deliver the substitution fluid. When the substitution pump 20 is stopped, the flow route of the flexible tube is closed.

The substitution line Lb according to the present embodiment is provided with the rubber button 16, serving as the infusion portion, at a position on the upstream side with respect to the substitution pump 20 (between the substitution pump 20 and the collecting port 11). The rubber button 16 allows a predetermined liquid drug that should be administered to the patient to be infused into the substitution line Lb. In the present embodiment, the distal end of the substitution line Lb is connected to the position of the venous blood circuit 3 that is between the dialyzer 1 and the venous air-trap chamber 6. Alternatively, the distal end of the substitution line Lb may be connected to any other position, such as another position of the venous blood circuit 3 or a predetermined position of the arterial blood circuit 2, as long as the position is defined in the blood circuit and on the downstream side with respect to the blood pump 4.

If a liquid drug needs to be administered to the patient in, for example, the middle or last phase of the blood purification treatment, a medical worker touches the starting portion 18*b* of the display 18, whereby the drug introduction mode is executed. When the drug introduction mode is executed, the blood pump 4 is temporarily stopped (see FIG. 5). Then, as illustrated in FIG. 14, the electromagnetic valves V1 and V2 are closed. Furthermore, with the electromagnetic valve V4 kept closed, the electromagnetic valve V3 is opened, whereby the control sequence proceeds to the bypassing step S1.

In the bypassing step S1, the flow routes that allow the dialysate to be introduced into the dialyzer 1 (the blood purification unit) through the dialysate introduction line L1 and discharged from the dialyzer 1 (the blood purification unit) into the drain-liquid discharge line L2 are closed (that is, the electromagnetic valves V1 and V2 are closed), whereby the dialysate is caused to flow through the bypass line L3. When the bypassing step S1 ends and the introduction of the dialysate into the dialyzer 1 and the discharge of the drain liquid from the dialyzer 1 are stopped, the introduction step S2 is executed.

In the introduction step S2 subsequent to the bypassing step S1, as illustrated in FIG. 15, the blood pump 4 is kept active, and the substitution pump 20 is activated, whereby the substitution fluid in the substitution line Lb is introduced into the blood circuit (in the present embodiment, the venous blood circuit 3), and the liquid drug infused from the rubber button 16 (the infusion portion) is thus introduced into the blood circuit together with the substitution fluid. Specifically, before the substitution pump 20 is activated, the flow route of the substitution line Lb is closed. However, with the activation of the substitution pump 20, the substitution fluid in the substitution line Lb is caused to flow into the blood circuit.

Before the execution of the introduction step S2, it is preferable to generate a positive pressure in a portion of the substitution line Lb that is on the upstream side with respect to the substitution pump 20 by activating the duplex pump 7. In such a case, the liquid drug infused to the portion on the upstream side with respect to the substitution pump 20 is retained near the substitution pump 20. Therefore, when the substitution pump 20 is activated, the liquid drug is delivered to the blood circuit (in the present embodiment, the venous blood circuit 3) without flowing backward to the dialysate introduction line L1. Furthermore, such a positive pressure generated in the portion of the substitution line Lb that is on the upstream side with respect to the substitution pump 20 also prevents the occurrence of backflow of the blood in the blood circuit (in the present embodiment, the venous blood circuit 3) through a gap in the substitution pump 20 (a gap that may be produced if the flexible tube is not fully closed by the rollers).

Accordingly, if a liquid drug to be administered to the patient is infused from the rubber button 16, the liquid drug thus infused is introduced into the blood circuit (the venous blood circuit 3) together with the substitution fluid in the substitution line Lb. Meanwhile, on the display 18, the volume of the substitution fluid introduced into the venous blood circuit 3 with the execution of the drug introduction mode is displayed in the substitution-volume display portion 18*c*, and the number of times of execution of the drug introduction mode is displayed in the number-of-executions display portion 18*d*.

Then, in S3, it is determined whether or not a preset volume of the substitution fluid (the substitution fluid containing the liquid drug) has been introduced from the substitution line Lb into the venous blood circuit 3 in the introduction step S2. If it is determined that the preset volume of the substitution fluid has been introduced, the sequence proceeds to S4, where the target ultrafiltration volume is corrected. To summarize, in the present embodiment, a target ultrafiltration volume for water removal from the patient's blood through the dialyzer 1 is settable. Furthermore, the calculation unit 19 calculates the volume of the substitution fluid introduced from the substitution line Lb into the venous blood circuit 3 (any position of the blood circuit that is on the downstream side with respect to the blood pump 4) with the execution of the drug introduction mode. Therefore, when the drug introduction mode is executed, the target ultrafiltration volume is corrected with the addition of the volume of the substitution fluid calculated by the calculation unit 19.

After the target ultrafiltration volume is corrected as above, the sequence proceeds to S5, where the mode is changed to the treatment mode illustrated in FIG. 13. Thus, the sequence of the drug introduction mode ends, and the mode is changed to the treatment mode to restart the blood purification treatment. In the blood purification treatment, as with the case of the first embodiment, the driving speed of the blood pump 4 is controlled to be higher than the driving speed in the drug introduction mode.

Now, a control sequence, executed by the control unit 17, according to a fifth embodiment will be described with reference to the flow chart illustrated in FIG. 16.

The present embodiment employs the substitution pump 20 and the substitution line Lb, which are the same as those employed by the fourth embodiment. In the blood purification treatment, as with the case of the fourth embodiment and as illustrated in FIG. 13, when the blood pump 4 and the duplex pump 7 are activated while a patient is punctured with the arterial puncture needle c and the venous puncture needle d, the patients blood is caused to extracorporeally circulate through the arterial blood circuit 2 and the venous blood circuit 3, whereby the blood undergoes the blood purification treatment in the dialyzer 1. In the blood purification treatment (the treatment mode), as illustrated in FIG. 13, the clamp unit Va (the arterial-blood-circuit opening-closing unit) and the clamp unit Vb are open, whereas the clamp unit Vc (the substitution-line opening-closing unit) and the electromagnetic valves V3 and V4 are closed.

If a liquid drug needs to be administered to the patient in, for example, the middle or last phase of the blood purification treatment, a medical worker touches the starting portion 18*b* of the display 18, whereby the drug introduction mode is executed. When the drug introduction mode is executed, as illustrated in FIG. 17, the substitution pump 20 is activated, whereby the introduction step S1 is executed. In this state, the electromagnetic valves V3 and V4 are closed, the electromagnetic valves V1 and V2 are open, and the duplex pump 7 is active. Therefore, the dialysate is introduced into the dialyzer 1 through the dialysate introduction line L1, and the resulting drain liquid is discharged from the dialyzer 1 into the drain-liquid discharge line L2. Furthermore, since the duplex pump 7 is active, the volume of the dialysate delivered through the dialysate introduction line L1 and the volume of the drain liquid delivered through the drain-liquid discharge line L2 are equal.

In the introduction step S1, the blood pump 4 is kept active, and the substitution pump 20 is activated, whereby the substitution fluid in the substitution line Lb is introduced into the blood circuit (in the present embodiment, the venous blood circuit 3), and the liquid drug infused from the rubber button 16 (the infusion portion) is thus introduced into the blood circuit together with the substitution fluid. Specifically, before the substitution pump 20 is activated, the flow route of the substitution line Lb is closed. However, with the activation of the substitution pump 20, the substitution fluid in the substitution line Lb is caused to flow into the blood circuit.

Before the execution of the introduction step S1, it is preferable to generate a positive pressure in a portion of the substitution line Lb that is on the upstream side with respect to the substitution pump 20 by activating the duplex pump 7. In such a case, the liquid drug infused to the portion on the upstream side with respect to the substitution pump 20 is retained near the substitution pump 20. Therefore, when the substitution pump 20 is activated, the liquid drug is delivered to the blood circuit (in the present embodiment, the venous blood circuit 3) without flowing backward to the dialysate introduction line L1. Furthermore, such a positive pressure generated in the portion of the substitution line Lb that is on the upstream side with respect to the substitution pump 20 also prevents the occurrence of backflow of the blood in the blood circuit (in the present embodiment, the venous blood circuit 3) through a gap in the substitution pump 20 (a gap that may be produced if the flexible tube is not fully closed by the rollers).

Accordingly, if a liquid drug to be administered to the patient is infused from the rubber button 16, the liquid drug thus infused is introduced into the blood circuit (the venous blood circuit 3) together with the substitution fluid in the substitution line Lb. Meanwhile, on the display 18, the volume of the substitution fluid introduced into the venous blood circuit 3 with the execution of the drug introduction mode is displayed in the substitution-volume display portion 18c, and the number of times of execution of the drug introduction mode is displayed in the number-of-executions display portion 18d.

In the present embodiment, since the duplex pump 7 is active, the volume of the dialysate delivered through the dialysate introduction line L1 and the volume of the drain liquid delivered through the drain-liquid discharge line L2 are equal. Therefore, when the drug introduction mode is executed, a volume of water that corresponds to the volume of the substitution fluid introduced into the venous blood circuit 3 in the introduction step S1 is removed through the dialyzer 1.

Specifically, when the substitution pump 20 is activated, some of the dialysate in the dialysate introduction line L1 flows into the substitution line Lb and reaches the venous blood circuit 3. Therefore, the volume of the dialysate introduced into the dialyzer 1 becomes smaller than the volume of the drain liquid by the volume of the dialysate flowing into the substitution line Lb. Consequently, a volume of water corresponding to the reduction is discharged from the dialyzer 1 into the drain-liquid discharge line L2. Therefore, when the drug introduction mode is executed, the volume of water that corresponds to the volume of the substitution fluid introduced into the venous blood circuit 3 in the introduction step S1 is naturally removed through the dialyzer 1.

Then, in S2, it is determined whether or not a preset volume of the substitution fluid (the substitution fluid containing the liquid drug) has been introduced from the substitution line Lb into the venous blood circuit 3 in the introduction step S1. If it is determined that the preset volume of the substitution fluid has been introduced, the sequence proceeds to S3, where the mode is changed to the treatment mode illustrated in FIG. 13. Thus, the sequence of the drug introduction mode ends, and the mode is changed to the treatment mode to restart the blood purification treatment. In the blood purification treatment, the driving speed of the blood pump 4 is controlled to be higher than the driving speed in the drug introduction mode.

According to each of the first to fifth embodiments, the blood purification apparatus includes the control unit that executes the drug introduction mode in which the substitution fluid in the substitution line (La, Lb) is introduced into the blood circuit, the control unit causing the liquid drug infused from the rubber button 16 (the infusion portion) in the drug introduction mode to be introduced into the blood circuit together with the substitution fluid; and the calculation unit that calculates the volume of the substitution fluid introduced from the substitution line (La, Lb) into the blood circuit with the execution of the drug introduction mode. Therefore, when a liquid drug is infused from the substitution line (La, Lb) into the blood circuit, the blood flowing in the blood circuit is prevented from flowing into the substitution line (La, Lb). Furthermore, medical workers are made aware of an appropriate timing of liquid drug infusion. Furthermore, since the blood purification apparatus includes the calculation unit 19 that calculates the volume of the substitution fluid introduced from the substitution line (La, Lb) into the blood circuit with the execution of the drug introduction mode, the volume of water that corresponds to the volume of the substitution fluid introduced into the patient's body with the execution of the drug introduction mode is identifiable for the ultrafiltration in the blood purification treatment.

In particular, according to each of the first to third embodiments, the drug introduction mode is executed, which includes the negative-pressure-generating step (the pressure-controlling step) of generating a negative pressure in the portion of the arterial blood circuit 2 that is between the distal part and the blood pump 4 by closing the clamp unit Vc (the substitution-line opening-closing unit) and the clamp unit Va (the arterial-blood-circuit opening-closing unit); the suction step of suctioning the substitution fluid in the substitution line La into the arterial blood circuit 2 by opening the clamp unit Va after the negative-pressure-generating step (the pressure-controlling step); and the introduction step of introducing the substitution fluid in the substitution line La into the arterial blood circuit 2 by activating the blood pump 4 after the suction step. Furthermore, the liquid drug infused from the rubber button 16 (the infusion portion) is suctioned or introduced into the arterial blood circuit 2 together with the substitution fluid in the suction step or the introduction step. Therefore, with the negative pressure generated when the liquid drug is infused from the substitution line La into the blood circuit, the blood flowing in the blood circuit is more assuredly prevented from flowing into the substitution line La.

According to each of the first to fifth embodiments, the control unit 17 executes the drug introduction mode if the predetermined starting operation is performed. Therefore, the liquid drug is infusible into the infusion portion with an arbitrary timing. According to each of the first to third embodiments, the control unit 17 causes the substitution fluid in the substitution line La to be introduced into the arterial blood circuit 2 by activating the blood pump 4 in the suction step for the generation of the negative pressure and by keeping the blood pump 4 active in the introduction step. Therefore, with the activation of the blood pump 4, the generation of the negative pressure in the negative-pressure-generating step (the pressure-controlling step) and the introduction of the substitution fluid in the introduction step are achieved successively.

According to the second embodiment, the target ultrafiltration volume for water removal from the blood of the patient through the dialyzer 1 is settable. Furthermore, when the drug introduction mode is executed, the target ultrafiltration volume is corrected with the addition of the volume of the substitution fluid calculated by the calculation unit 19. Therefore, the volume of water that corresponds to the volume of the substitution fluid introduced into the patient's body with the execution of the drug introduction mode is automatically removed in the blood purification treatment.

According to each of the first, second, and fourth embodiments, the substitution line (La, Lb) is connected to the dialysate introduction line L1 and to the blood circuit in such a manner as to allow the dialysate in the dialysate introduction line L1 to be introduced as the substitution fluid into the blood circuit. Furthermore, when the drug introduction mode is executed, the control unit 17 executes the bypassing step in which the control unit 17 causes the dialysate to flow through the bypass line L3 by closing the flow routes that allow the dialysate to be introduced into the dialyzer 1 through the dialysate introduction line L1 and discharged from the dialyzer 1 into the drain-liquid discharge line L2. Therefore, the liquid drug is prevented from being discharged from the dialyzer 1 into the drain-liquid discharge line L2.

According to each of the third and fifth embodiments, the substitution line (La, Lb) is connected to the dialysate introduction line L1 and to the blood circuit in such a manner as to allow the dialysate in the dialysate introduction line L1 to be introduced as the substitution fluid into the blood circuit. Furthermore, when the drug introduction mode is executed, the control unit 17 causes a volume of water that corresponds to the volume of the substitution fluid introduced into the blood circuit in the suction step or the introduction step to be removed through the dialyzer 1. Therefore, the volume of water that corresponds to the volume of the substitution fluid suctioned or introduced into the blood circuit with the execution of the drug introduction mode is removed through the dialyzer 1.

In particular, according to each of the third and fifth embodiments, the blood purification apparatus includes the duplex pump 7 provided astride the dialysate introduction line L1 and the drain-liquid discharge line L2 and that delivers the dialysate in the dialysate introduction line L1 to the drain-liquid discharge line L2, the duplex pump 7 equalizing the volume of the dialysate to be delivered through the dialysate introduction line L1 and the volume of the drain liquid to be delivered through the drain-liquid discharge line L2. Therefore, when the duplex pump 7 is activated, the volume of water that corresponds to the volume of the substitution fluid suctioned or introduced into the blood circuit with the execution of the drug introduction mode is naturally removed through the dialyzer 1.

According to each of the first to fifth embodiments, if the blood purification apparatus is configured to display an indication that prompts the execution of the drug introduction mode or an indication that prompts the infusion of the liquid drug from the rubber button 16 (the infusion portion), medical workers are prevented from forgetting to start the drug introduction mode or to infuse the liquid drug from the rubber button 16. Furthermore, when the drug introduction mode is executed, the volume of the substitution fluid introduced from the substitution line (La, Lb) into the blood circuit or the number of times of infusion of the liquid drug from the rubber button 16 (the infusion portion) is displayed. Therefore, medical workers are correctly made aware of the volume of the substitution fluid or the number of times of infusion of the liquid drug.

According to each of the fourth and fifth embodiments, the blood purification apparatus includes the substitution pump 20 provided to the substitution line Lb and that delivers the substitution fluid to the blood circuit. Furthermore, the control unit 17 executes the drug introduction mode by executing the introduction step of introducing the substitution fluid in the substitution line Lb into the blood circuit by activating the substitution pump 20. Furthermore, the liquid drug infused from the rubber button 16 (the infusion portion) is introduced into the blood circuit together with the substitution fluid in the introduction step. Therefore, when the liquid drug is infused from the substitution line Lb into the blood circuit, the activation of the substitution pump 20 prevents the blood in the blood circuit from flowing into the substitution line Lb. Furthermore, medical workers are made aware of an appropriate timing of liquid drug infusion.

While some embodiments have been described above, the present invention is not limited thereto. For example, the timing of liquid drug infusion from the rubber button 16 is not limited to a point in the suction step or the introduction step (that is, after the clamp unit Vc (the substitution-line opening-closing unit) is opened in the suction step) as in the above embodiments. The liquid drug may be infused from the rubber button 16 before the suction step. In that case, as illustrated in FIG. 20, the above substitution line La may be replaced with a substitution line La', which is connected to a bag containing physiological saline serving as the substitution fluid and allows the physiological saline as the substitution fluid to be introduced into the arterial blood circuit 2 by opening the clamp unit Vc (the substitution-line opening-closing unit).

Alternatively, as illustrated in FIG. 21, the blood purification apparatus may include an air-trap chamber D provided at the connection between the arterial blood circuit 2 and the substitution line La, and a liquid-level-adjusting pump M that adjusts the surface level of a liquid layer in the air-trap chamber D by introducing or discharging air into or from an air layer in the air-trap chamber D. Furthermore, the control unit 17 may activate the liquid-level-adjusting pump M together with or instead of the blood pump 4 in the suction step.

In such a case, the negative pressure to be generated in the negative-pressure-generating step (the pressure-controlling step) may be generated by utilizing the liquid-level-adjusting pump M, which is intended for the adjustment of the liquid level in the air-trap chamber D. In FIG. 21, reference signs Vd and S respectively denotes a clamp unit provided to a flow route for the introduction or discharge of air into or from the air-trap chamber D, and a pressure-measurement unit for measuring the pressure in the flow route.

Furthermore, it is preferable that a volume of water that corresponds to the volume of the substitution fluid calculated by the calculation unit 19 be removed from the blood of the patient through the dialyzer 1 (the blood purification unit). In such a case, the ultrafiltration by the dialyzer 1 may be executed either in the drug introduction mode or in the treatment mode. In either mode, the volume of water corresponding to the volume of the substitution fluid introduced into the patient's body together with the liquid drug is removed assuredly.

Furthermore, the negative-pressure-generating step (the pressure-controlling step) is not limited to a step of generating a negative pressure and only needs to be a step of controlling, when the drug introduction mode is executed, the pressure at the connection between the blood circuit (the arterial blood circuit 2 or the venous blood circuit 3) and the substitution line (La or Lb) to be equal to or lower than the fluid pressure in the substitution line (La or Lb). For example, in each of the first to third embodiments, the fluid pressure may be controlled with reference to the atmospheric pressure (0 kPa) by closing the clamp unit Va (the arterial-blood-circuit opening-closing unit) and the clamp unit Vc (the substitution-line opening-closing unit) to establish a closed system and then rotating the blood pump 4 normally or reversely. Alternatively, in each of the fourth and fifth embodiments, since the portion of the substitution line Lb that is on the upstream side with respect to the substitution pump 20 forms a closed system filled with the dialysate, the pressure is controllable by controlling the driving speed of the duplex pump 7. To summarize, if the pressure at the connection between the blood circuit and the substitution line Lb is controlled by the control unit 17 at the execution of the drug introduction mode, the occurrence of backflow of the blood into the substitution line Lb is avoided.

The present teachings are also applicable to a blood purification apparatus having additional functions or the like, as long as the apparatus includes a control unit that executes a drug introduction mode in which a substitution fluid in a substitution line is introduced into a blood circuit, the control unit causing a liquid drug infused from an infusion portion in the drug introduction mode to be introduced into the blood circuit together with the substitution fluid; and a calculation unit that calculates a volume of the substitution fluid introduced from the substitution line into the blood circuit with the execution of the drug introduction mode.

REFERENCE SIGN LIST

1 dialyzer (blood purification unit)
2 arterial blood circuit
3 venous blood circuit
4 blood pump
5 arterial air-trap chamber
6 venous air-trap chamber
7 duplex pump
8, 9 filter
10 ultrafiltration pump
11 collecting port
12 fluid-pressure measurement sensor
13 venous-pressure sensor
14 pressurizing pump
15 degassing chamber
16 rubber button (infusion portion)
17 control unit
18 display
19 calculation unit
20 substitution pump
L1 dialysate introduction line
L2 drain-liquid discharge line
L3 bypass line
L4 bypass line
L7 atmosphere release line
La, Lb substitution line
B dialysis device
Va clamp unit (arterial-blood-circuit opening-closing unit)
Vc clamp unit (substitution-line opening-closing unit)
a, b connector

What is claimed is:

1. A blood purification apparatus that includes
a blood circuit including an arterial blood circuit and a venous blood circuit and through which blood of a patient is allowed to extracorporeally circulate;
a blood purification unit connected to and provided between the arterial blood circuit and the venous blood circuit and that purifies the blood flowing through the blood circuit;
a blood pump provided to the arterial blood circuit and that delivers the blood of the patient from the arterial blood circuit through the blood purification unit to the venous blood circuit;
a substitution line through which a substitution fluid is allowed to be introduced into the blood circuit; and
an infusion portion attached to the substitution line and from which a predetermined liquid drug to be administered to the patient is allowed to be infused into the substitution line, wherein the infusion portion is made of rubber and the infusion portion is configured to allow the predetermined liquid drug to be infused by medical workers;
the blood purification apparatus comprising:
a display;
a control unit that executes a drug introduction mode, when a starting portion of the display is actuated, in which the substitution fluid in the substitution line is introduced into the blood circuit, the control unit causing the predetermined liquid drug infused from the infusion portion in the drug introduction mode to be introduced into the blood circuit together with the substitution fluid, wherein the control unit upon execution of the drug introduction mode, a volume of the substitution fluid introduced to the blood circuits is displayed on the display as a substitution-volume of a substitution-volume display portion of the display;
a calculation unit that calculates:
the volume of the substitution fluid introduced from the substitution line into the blood circuit with the execution of the drug introduction mode; and
a target ultrafiltration volume for water removal from the blood of the patient that flows through the blood purification unit with an ultrafiltration pump, is settable, and the control unit corrects the target ultrafiltration volume an addition of the volume of water that corresponds to the volume of the substitution fluid calculated by the calculation unit to the target ultrafiltration volume, and removes water from the patient's blood through the blood purification unit by activating the ultrafiltration pump based on the target ultrafiltration volume after correction;
wherein the display provides an indication that prompts the medical workers to execute the drug introduction mode.

2. The blood purification apparatus according to claim 1, wherein when the drug introduction mode is executed, the control unit controls a pressure at a connection between the blood circuit and the substitution line to be equal to or lower than a fluid pressure in the substitution line.

3. The blood purification apparatus according to claim 1, further comprising:

an arterial-blood-circuit opening-closing unit provided in the arterial blood circuit and that is capable of arbitrarily opening or closing an arterial circuit flow route; and a substitution-line opening-closing unit provided between the substitution line and the arterial blood circuit and that is capable of arbitrarily opening or closing a substitution-line flow route, wherein the control unit executes the drug introduction mode by executing a negative-pressure-generating step of generating a negative pressure in a portion of the arterial blood circuit by closing the substitution-line opening-closing unit and the arterial-blood-circuit opening-closing unit so that a negative pressure is generated in the arterial blood circuit by the blood pump moving the substitution fluid through the arterial blood circuit;

a suction step of suctioning the substitution fluid in the substitution line into the arterial blood circuit by opening the substitution-line opening-closing unit after the negative-pressure-generating step so that the blood pump moves the fluid into the arterial blood circuit; and an introduction step of introducing the substitution fluid in the substitution line into the arterial blood circuit by activating the blood pump after the suction step, and wherein the predetermined liquid drug infused from the infusion portion is suctioned or introduced into the blood circuit together with the substitution fluid in the suction step or the introduction step.

4. The blood purification apparatus according to claim 1, wherein the control unit executes the drug introduction mode when a predetermined starting operation is performed by introducing a volume of the substitution fluid from the substitution line into the arterial blood circuit with an introduction of a drug during the drug introduction mode.

5. The blood purification apparatus according to claim 3, wherein the control unit causes the substitution fluid in the substitution line to be introduced into the arterial blood circuit by activating the blood pump in the suction step for the generation of the negative pressure and by keeping the blood pump active in the introduction step.

6. The blood purification apparatus according to claim 3, further comprising:
an air-trap chamber provided at the connection between the arterial blood circuit and the substitution line; and
a liquid-level-adjusting pump that adjusts a surface level of a liquid layer in the air-trap chamber by introducing or discharging air into or from an air layer in the air-trap chamber,
wherein the control unit generates the negative pressure by activating the liquid-level-adjusting pump together with or instead of the blood pump in the suction step.

7. The blood purification apparatus according to claim 1, further comprising a substitution pump provided to the substitution line and that delivers the substitution fluid to the blood circuit, wherein the control unit executes the drug introduction mode by executing an introduction step of introducing the substitution fluid in the substitution line into the blood circuit by activating the substitution pump, and wherein the predetermined liquid drug infused from the infusion portion is introduced into the blood circuit together with the substitution fluid in the introduction step.

8. The blood purification apparatus according to claim 1, wherein the target ultrafiltration volume is corrected when the drug introduction mode is executed.

9. The blood purification apparatus according to claim 1, further comprising:

a dialysate introduction line through which dialysate is introduced into the blood purification unit;
a drain-liquid discharge line into which drain liquid from the blood purification unit is discharged; and
a bypass line connected to and communicating with the dialysate introduction line and the drain-liquid discharge line and through which the dialysate in the dialysate introduction line is allowed to bypass the blood purification unit and flow into the drain-liquid discharge line,
wherein the substitution line is connected to the dialysate introduction line and to the blood circuit in such a manner as to allow the dialysate in the dialysate introduction line to be introduced as the substitution fluid into the blood circuit, and wherein when the drug introduction mode is executed, the control unit executes a bypassing step in which the control unit causes the dialysate to flow through the bypass line by closing flow routes that allow the dialysate to be introduced into the blood purification unit through the dialysate introduction line and discharged from the blood purification unit into the drain-liquid discharge line.

10. The blood purification apparatus according to claim 1, further comprising:
a dialysate introduction line through which dialysate is introduced into the blood purification unit; and
a drain-liquid discharge line into which drain liquid from the blood purification unit is discharged,
wherein the substitution line is connected to the dialysate introduction line and to the blood circuit in such a manner as to allow the dialysate in the dialysate introduction line to be introduced as the substitution fluid into the blood circuit, and wherein when the drug introduction mode is executed, the control unit causes a volume of water that corresponds to the volume of the substitution fluid introduced into the blood circuit to be removed through the blood purification unit.

11. The blood purification apparatus according to claim 10, further comprising a duplex pump provided astride the dialysate introduction line and the drain-liquid discharge line and that delivers the dialysate in the dialysate introduction line to the drain-liquid discharge line, the duplex pump equalizing a volume of the dialysate to be delivered through the dialysate introduction line and a volume of the drain liquid to be delivered through the drain-liquid discharge line.

12. The blood purification apparatus according to claim 1, wherein when the drug introduction mode is executed, the volume of the substitution fluid introduced from the substitution line into the blood circuit or a number of times of infusion of the predetermined liquid drug from the infusion portion is displayed.

13. The blood purification apparatus according to claim 3, wherein the negative pressure is generated in the arterial blood circuit in a portion between an end of the arterial blood circuit and the blood pump.

14. The blood purification apparatus according to claim 1, wherein the infusion portion is a rubber button that is pierceable by a syringe so that the predetermined liquid drug is introduced through the rubber button.

15. The blood purification apparatus according to claim 1, further comprising:
a clamp unit located in the substitution line between the infusion portion and the arterial blood circuit.

16. The blood purification apparatus according to claim 15, further comprising:

an electromagnetic valve located in the arterial blood circuit, wherein the substitution line provides substitution fluid into the arterial blood circuit between the electromagnetic valve and the blood pump.

\* \* \* \* \*